(12) United States Patent
Duerksen et al.

(10) Patent No.: US 10,127,447 B2
(45) Date of Patent: *Nov. 13, 2018

(54) SYSTEM AND METHOD FOR AUTHENTICATION

(71) Applicant: ClearMark Systems, LLC, Longmont, CO (US)

(72) Inventors: Gary L. Duerksen, Ward, CO (US); Seth A. Miller, Longmont, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/981,888

(22) Filed: Dec. 28, 2015

(65) Prior Publication Data

US 2016/0196472 A1    Jul. 7, 2016

Related U.S. Application Data

(63) Continuation of application No. 14/656,705, filed on Mar. 12, 2015, now Pat. No. 9,224,196.

(Continued)

(51) Int. Cl.
*G06F 17/00* (2006.01)
*G06K 9/00* (2006.01)
(Continued)

(52) U.S. Cl.
CPC ..... *G06K 9/00577* (2013.01); *G01N 21/9501* (2013.01); *G06K 9/18* (2013.01);
(Continued)

(58) Field of Classification Search
CPC ....... G06K 9/00577; G06K 2009/0059; G06K 9/46; G06K 9/4604; G06K 9/18;
(Continued)

(56) References Cited

U.S. PATENT DOCUMENTS 5,267,332 A * 11/1993 Walch ................ G06K 9/4638
382/198
5,719,948 A * 2/1998 Liang ..................... G06K 7/12
283/72
(Continued)

FOREIGN PATENT DOCUMENTS

WO    WO 2015071442 A1 *  5/2015   ......... G06K 9/00577

OTHER PUBLICATIONS

International Search Report and the Written Opinion of the International Searching Authority for related application PCT/US15/20309, dated Jun. 15, 2015.
(Continued)

*Primary Examiner* — Paultep Savusdiphol
(74) *Attorney, Agent, or Firm* — Benesch Friedlander Coplan & Aronoff LLP; Kraig K. Anderson

(57) ABSTRACT

Described are methods and systems for determining authenticity. For example, the method may include providing an object of authentication, capturing characteristic data from the object of authentication, deriving authentication data from the characteristic data of the object of authentication, and comparing the authentication data with an electronic database comprising reference authentication data to provide an authenticity score for the object of authentication. The reference authentication data may correspond to one or more reference objects of authentication other than the object of authentication.

12 Claims, 20 Drawing Sheets

Related U.S. Application Data

(60) Provisional application No. 61/952,122, filed on Mar. 12, 2014.

(51) Int. Cl.

| | | |
|---|---|---|
| *G06T 7/00* | (2017.01) | |
| *G06K 9/46* | (2006.01) | |
| *G06K 9/18* | (2006.01) | |
| *G09G 5/24* | (2006.01) | |
| *G01N 21/95* | (2006.01) | |
| *G07D 7/00* | (2016.01) | |
| *G07D 7/12* | (2016.01) | |
| *G07D 7/20* | (2016.01) | |

(52) U.S. Cl.
CPC ............ *G06K 9/4604* (2013.01); *G06T 7/001* (2013.01); *G06T 7/0002* (2013.01); *G07D 7/00* (2013.01); *G07D 7/12* (2013.01); *G07D 7/20* (2013.01); *G09G 5/24* (2013.01); *G06K 2009/0059* (2013.01); *G06K 2209/01* (2013.01); *G06K 2209/19* (2013.01); *G06T 2207/10024* (2013.01); *G06T 2207/30148* (2013.01)

(58) Field of Classification Search
CPC ...... G07D 7/20; G07D 7/2025; G06T 7/0002; G09G 5/24
USPC .................... 235/454, 375, 472.01
See application file for complete search history.

(56) References Cited

U.S. PATENT DOCUMENTS

| | | | |
|---|---|---|---|
| 5,787,186 A | 7/1998 | Schroeder | |
| 6,373,965 B1* | 4/2002 | Liang ................. | B41M 3/144 382/112 |
| 6,533,181 B1 | 3/2003 | Roxby et al. | |
| 7,152,786 B2* | 12/2006 | Brundage ............ | G06K 19/16 235/380 |
| 7,599,544 B2* | 10/2009 | Moshe ................. | G07D 7/122 356/456 |
| 2004/0188528 A1 | 9/2004 | Alasia et al. | |
| 2004/0189663 A1 | 9/2004 | Perry et al. | |
| 2004/0223197 A1* | 11/2004 | Ohta ................. | G06F 17/30271 358/538 |
| 2005/0100992 A1 | 5/2005 | Noble | |
| 2005/0197926 A1 | 9/2005 | Chinnappan et al. | |
| 2006/0074986 A1* | 4/2006 | Mallalieu ........... | G07C 9/00087 |
| 2006/0114485 A1* | 6/2006 | Sato ................. | G06F 17/30271 358/1.13 |
| 2006/0161788 A1* | 7/2006 | Turpin ................ | G06K 9/4652 713/186 |
| 2006/0202470 A1* | 9/2006 | Simske ............ | G06K 19/06037 283/74 |
| 2006/0210162 A1* | 9/2006 | Sato ................. | G06F 17/30247 382/176 |
| 2006/0221357 A1* | 10/2006 | Uzawa ................ | G06F 17/3028 358/1.1 |
| 2007/0071323 A1* | 3/2007 | Kontsevich ....... | G06F 17/30247 382/190 |
| 2007/0187266 A1 | 8/2007 | Porter et al. | |
| 2008/0002882 A1* | 1/2008 | Voloshynovskyy ........................ | G07D 7/0046 382/181 |
| 2008/0173714 A1* | 7/2008 | Kite .......................... | B07C 3/00 235/386 |
| 2008/0192992 A1* | 8/2008 | Moshe ................... | G07D 7/122 382/124 |
| 2008/0294900 A1* | 11/2008 | Cowburn ........... | G06K 9/00577 713/176 |
| 2009/0003700 A1 | 1/2009 | Xiao | |
| 2009/0067691 A1* | 3/2009 | Sato .................... | G06K 9/00026 382/124 |
| 2009/0128858 A1* | 5/2009 | Kiuchi ..................... | G07D 7/20 358/3.28 |
| 2010/0073735 A1* | 3/2010 | Hunt ..................... | G06T 3/0031 358/462 |
| 2010/0157318 A1* | 6/2010 | Ming ................... | G07D 7/2025 358/1.1 |
| 2010/0200649 A1* | 8/2010 | Callegari ............. | G06K 19/086 235/375 |
| 2011/0096955 A1 | 4/2011 | Voloshynovskiy et al. | |
| 2011/0258130 A1* | 10/2011 | Grabiner .............. | G06Q 10/087 705/317 |
| 2012/0061470 A1* | 3/2012 | Marguerettaz ... | G06K 19/06046 235/454 |
| 2012/0327450 A1* | 12/2012 | Sagan .................. | G03G 21/046 358/1.14 |
| 2013/0142440 A1* | 6/2013 | Hirayama .......... | G06K 9/00496 382/212 |
| 2013/0173383 A1* | 7/2013 | Sharma .............. | G06Q 30/0201 705/14.47 |
| 2013/0181435 A1* | 7/2013 | Hersch ................. | H04N 1/6058 283/85 |
| 2013/0191389 A1* | 7/2013 | Lazarevic .......... | G06K 9/00463 707/737 |
| 2014/0122889 A1* | 5/2014 | Freund ................ | G01S 19/14 713/176 |
| 2014/0168426 A1* | 6/2014 | Andres ................ | G07D 7/122 348/143 |
| 2014/0285855 A1* | 9/2014 | Capobianco ............ | B41M 3/14 358/3.28 |

OTHER PUBLICATIONS

Sanjana, et al., "An Automated Recognition of Fake or Destroyed Indian Currency Notes in Machine Vision," International Journal of Computer Science & Management Studies, 2012, v. 12, pp. 2231-5268.

Shariati et al., "Randomly Driven Fuzzy Key Extraction of Unclonable Images," Proceedings, 2010 17th IEEE International Conference on Image Processing (ICIP), Hong Kong, pp. 1-4, 10.1109/ICIP.2010.5652420.

* cited by examiner

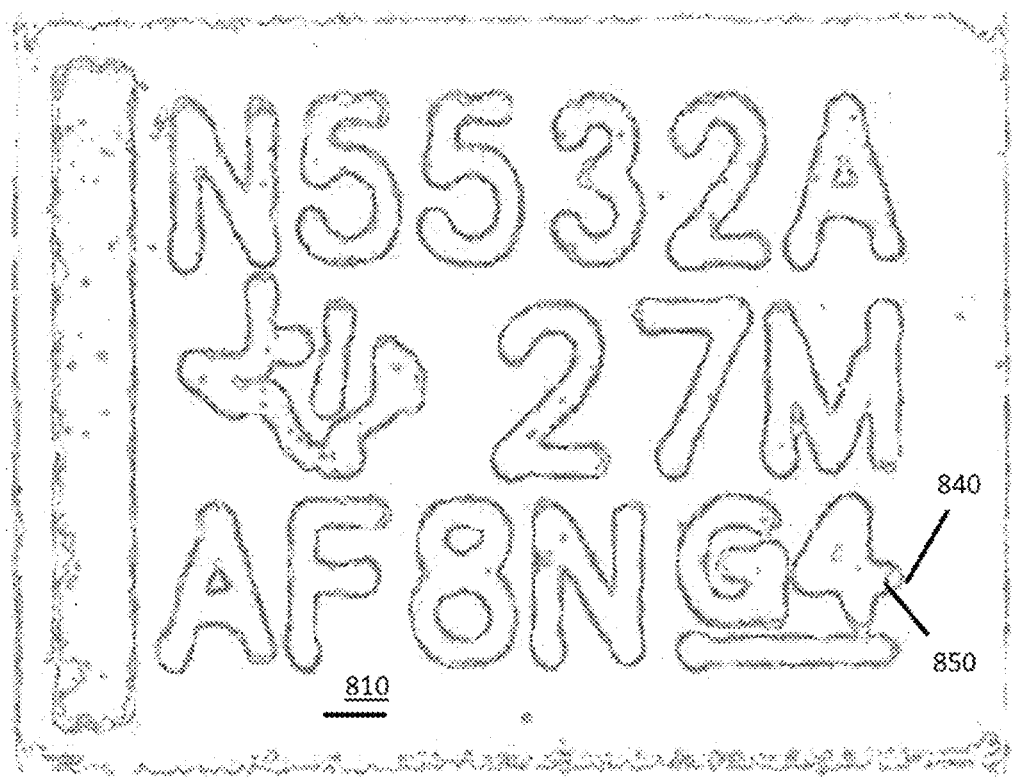
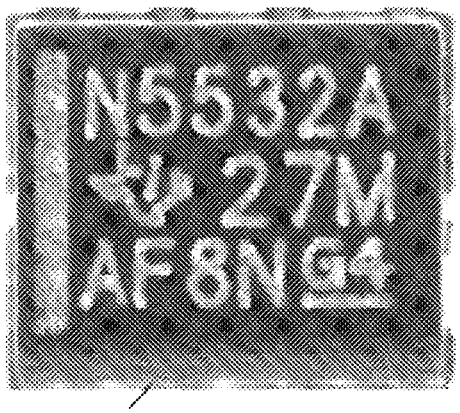
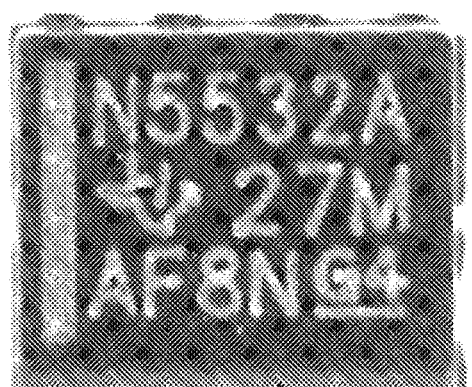
FIG. 8

1900

1902
INSTRUCTIONS FOR CONTROLLING A PROCESSOR TO:

OPERATE THE CHARACTERIZATION MODULE TO CAPTURE THE CHARACTERISTIC DATA FROM THE OBJECT OF AUTHENTICATION;

DERIVE AUTHENTICATION DATA FROM THE CHARACTERISTIC DATA OF THE OBJECT OF AUTHENTICATION;

COMPARE THE AUTHENTICATION DATA WITH THE ELECTRONIC DATABASE INCLUDING THE REFERENCE AUTHENTICATION DATA TO PROVIDE AN AUTHENTICITY SCORE FOR THE OBJECT OF AUTHENTICATION;

ACCESS THE DATA STORAGE MODULE TO STORE AND RETRIEVE ONE OR MORE OF: THE AUTHENTICATION DATA, THE ELECTRONIC DATABASE INCLUDING THE REFERENCE AUTHENTICATION DATA, THE CHARACTERISTIC DATA FROM THE OBJECT OF AUTHENTICATION, AND THE AUTHENTICITY SCORE.

FIG. 19

SYSTEM AND METHOD FOR AUTHENTICATION

CROSS-REFERENCE TO RELATED APPLICATIONS

This application claims priority to U.S. patent application Ser. No. 14/656,705, filed on Mar. 12, 2015, and U.S. Provisional Patent Application No. 61/952,122, filed on Mar. 12, 2014, each of which is entirely incorporated herein by reference.

STATEMENT AS TO RIGHTS TO INVENTIONS MADE UNDER FEDERALLY-SPONSORED RESEARCH AND DEVELOPMENT

This invention was made with Government support under Contract W911NF-14-C-0038 awarded by the U.S. Department of Energy. The Government may have certain rights in the invention.

BACKGROUND

Semiconductors and other high technology items, pharmaceuticals, entertainment media and fabricated consumer goods such as handbags may be subject to high degrees of counterfeiting. Counterfeit items may incur billions of dollars in lost revenue to manufacturers, result in legal actions, and for critical systems may compromise communication security or result in loss of life.

In the field of electronics, counterfeit semiconductor devices may generally be less expensive substitutes, salvaged scrap parts, or even non-functional semiconductor devices that do not meet the performance and/or quality specifications of non-counterfeit semiconductor devices. For example, "standard" semiconductor devices may be substituted for higher reliability or performance "mil-spec" semiconductor devices. Semiconductor device counterfeiting may be a significant concern in supply chains where semiconductor devices are not shipped from the manufacturer through trusted intermediaries to customers in real time. This may often be the case with low-run or end-of-life semiconductor devices where products may enter the supply chain when semiconductor devices from a trusted source cannot be obtained in a timely manner, at an appropriate cost, or at all. This so-called "gray-market" for semiconductor devices is outside of traditional supply chain management practices and controls, and may represent significant risk to the producers of systems that incorporate such semiconductor devices. The Semiconductor Industry Association estimates that the total damage done by semiconductor device counterfeiting exceeds $7.5 billion annually, with the bulk of this economic damage done to the final product owners who must recall or repair integrated systems to repair the intrusion of sub-par semiconductor devices into their supply chain.

Multiple common methods exist for ensuring the authenticity and/or provenance of objects, for example: supply chain management, anti-counterfeit tagging, and inspection for determination of provenance. The method of secure supply chain management controls the flow of objects from factory to end user and is regimented by a quality system. Objects transferred under this method are often tracked using printed text and barcode labels or RFID tags. As long as the transfer of objects is as prescribed by the quality system, the objects are assumed to be securely transferred and therefore genuine. However, supply chains may be stressed by events such as natural disasters, may be breached by unscrupulous parties, and may be difficult to maintain for many lower volume manufactured objects; thus, this solution does not fully meet the needs of multiple industries requiring genuine objects or those of known provenance.

The method of anti-counterfeit tagging adds to objects, often at the time of manufacture, features, characteristics, and/or identifiers that are difficult or impossible to counterfeit. Multiple proprietary tagging systems exist today, including schemes that incorporate microparticles, holograms, specialized inks, microprinting, DNA marking, fluorescent particles and/or IR inks. These anti-counterfeiting tagging systems are considered secure since they are hard to duplicate because they require complex processes for both creation and verification. These anti-counterfeiting tagging systems often represent security codes with billions of possible combinations, where a counterfeiter may not be able to properly guess a specific secret value.

Many of these proprietary anti-counterfeit tagging methods have problems such as: 1) manufacturing processes must change to incorporate these features, and 2) many methods require special systems to test for the authentication features. Each of these problems incur increased costs and difficulty for users and integrators and therefore inhibit adoption. For example, in the case of recent paper currency design changes, automatic bill-changers had to shift from magnetic sensing technology to optical and/or other sensing technologies to permit identification and authentication of the new styles of paper currency. Such changes can be mandated by a sole supplier of an object, in the case of paper currency a government as the only valid producer of its currency, but are difficult to implement in an industry with many varied suppliers and users of an object.

The method of inspection for determination of provenance utilizes inspection of object coloration, weight, visual markings, and/or other observables to authenticate objects. Although such inspection methods can capture the products of unsophisticated counterfeiters who are not attempting to properly replicate an object in detail; their overall capability is limited and as counterfeiters become increasingly sophisticated this method is of decreasing value. Ultimately, the limits of visual inspection can be traced back to the limits of the human eye or typical machine vision inspection system. These systems lack significant resolving power compared to the resolution of the tools used to create the visual markings and as a result, visually inspected counterfeit objects may incorrectly be deemed genuine or of known provenance.

Recently, the problem of counterfeiting is being addressed for semiconductor devices with the advent of inspections for a Physically Unclonable Function (PUF). A PUF is a representation of one or more physical features of an object that are easy to evaluate but impossible to control, even with knowledge of the exact manufacturing process that produced the object. An ideal PUF may be fabricated by a manufacturing process that creates features so difficult to control that they serve the function of a random number generator, where the number is permanently associated with each individual object and no other. Each object is thus assigned an effective serialization without the need for an exogenous taggant. After inspection, at the time of manufacture, the unique feature of the inspected object is stored in a database for comparison by subsequent inspection at a later time. With a properly selected PUF, billions if not trillions of discrete objects can be uniquely identified, and are essentially impossible to spoof.

For example, in a defined location of a specific sheet of paper, the fibers of cellulose may be arranged in a unique pattern that differs from the pattern that may be at that location in any other sheet of paper. There is no aspect of paper-making which controls the exact distribution of fibers, and thus from a manufacturing process the exact arrangement of fibers observed in any specific sheet of paper can be considered random and therefore unclonable, a PUF. An inspection process for this PUF using high resolution imaging and image analysis therefore inspects this feature and determines the effective serialization for each individual sheet of paper, and this physical feature is constant over the paper's life and therefore can be used to authenticate it.

A PUF may therefore provide a high degree of security; however, use of a PUF comes with significant complexity. The requirement for 100% inspection of objects at their time of production places significant burden and cost on the manufacturer of an object. This burden is further amplified when inspection techniques with low throughput are used, as they can easily create a bottleneck in the manufacturing line which makes production of objects uneconomical. Further, the requirement for 100% inspection results in a system that is vulnerable to supply chain errors since each object must be individually recorded. Finally, true PUFs can be difficult to identify and implement, since they require very large numbers of possible combinations (to remove the chance of repetition of serialization) and require consistency of inspection over all environmental conditions, and throughout the object's life.

For many applications there is simply no need to record a serialization for each individual object. For example, in many cases it is desirable to determine the authenticity or provenance of an object as Boolean state (genuine or not), but not necessarily establish its exact unique identity out of a very large collection of nominally identical objects. For example, the integrator of a semiconductor chip package need not unique identify each semiconductor chip package but desires to confirm the authenticity or provenance of a lot of such semiconductor chip packages. Thus, for these applications, which represent the majority of authentication requests, the benefits of a PUF are not valued while the costs necessary for implementation are high.

Previous work has also suggested the use of neural network vision systems for analysis of the authenticity of an object, most notably currency. Neural networks have been heavily studied for the extraction of information from complex visual images, and are especially useful in instances where it may be uncertain where the information resides. For example, a neural network has been previously developed to aid in the discrimination of photocopied bank notes from authentic notes. In this work, the neural net was trained using several hundred samples of known authentic notes and known forgeries, and developed a "hidden" algorithm to discriminate the two.

A weakness of neural networks, however, may be that their variables are hidden, and as a result when they fail it can be difficult to discern why. Although neural networks are powerful tools for analysis of complex images, they can be fragile when exposed to data outside their training sets. Further, because they are naïve about the location of information in an image, they require training with hundreds or thousands of data sets, which can be prohibitively expensive in many applications. Finally, because they use hidden algorithms and lack an explicit reference that serves as the basis for differentiation of authentic versus counterfeit items, they are not auditable by customers or standards bodies that wish to validate their performance.

There thus remains a significant need for new anti-counterfeiting, authenticity and provenance determination techniques which provide a required degree of security for objects that are both simple to operate and low cost, so that authentication tracking and control can be performed throughout the supply chain of the object.

SUMMARY

In one embodiment, a method for determining authenticity is provided. The method may include providing an object of authentication. The method may include capturing characteristic data from the object of authentication. The method may include deriving authentication data from the characteristic data of the object of authentication. The method may include comparing the authentication data with an electronic database including reference authentication data to provide an authenticity score for the object of authentication. The reference authentication data may correspond to one or more reference objects of authentication other than the object of authentication.

In another embodiment, a method for creating an electronic database is provided. The method may include providing at least one plurality of reference objects of authentication collectively belonging to a class. The method may include capturing characteristic data from the at least one plurality of reference objects of authentication. The method may include deriving reference authentication data from the characteristic data of the at least one plurality of reference objects of authentication. The method may include preparing the electronic database corresponding to the reference authentication data. The electronic database may include a representation of the class according to the at least one plurality of reference objects of authentication.

In one embodiment, a method for defining authentication data is provided. The method may include providing a first plurality of objects of authentication. The first plurality of objects of authentication may belong to a first family. The method may include capturing a plurality of characteristic data from the plurality of objects of authentication belonging to the first family. The method may include deriving a plurality of authentication data from the plurality of characteristic data. The method may include analyzing the plurality of authentication data to determine one or more authentication parameters. The one or more authentication parameters may be suitable for associating the plurality of objects of authentication with another object of authentication belonging to the first family. The one or more authentication parameters may be suitable for discriminating the plurality of objects of authentication of the first family from a second plurality of objects of authentication belonging to a second family.

In another embodiment, a system for determining authenticity is provided. The system may include a characterization module configured for capturing characteristic data from an object of authentication. The system may include a data storage module configured to store an electronic database including reference authentication data. The system may include a processor operatively coupled to the characterization module and the data storage module. The processor may be programmed to operate the characterization module to capture the characteristic data from the object of authentication. The processor may be programmed to derive authentication data from the characteristic data of the object of authentication. The processor may be programmed to compare the authentication data with the electronic database including the reference authentication data to provide an authenticity score for the object of authentication. The processor may be programmed to access the data storage module to store and retrieve one or more of: the authentication data, the electronic database including the reference authentication data, the characteristic data from the object of authentication, and the authenticity score.

In one embodiment, a tangible computer-readable medium having instructions stored thereon for controlling a processor is provided. The instructions may control the processor to operate the characterization module to capture the characteristic data from the object of authentication. The instructions may control the processor to derive authentication data from the characteristic data of the object of authentication. The instructions may control the processor to compare the authentication data with the electronic database including the reference authentication data to provide an authenticity score for the object of authentication. The instructions may control the processor to access the data storage module to store and retrieve one or more of: the authentication data, the electronic database including the reference authentication data, the characteristic data from the object of authentication, and the authenticity score.

In an embodiment, a method for determining the authenticity of a marked object includes providing a marked object for authentication, capturing characteristic data from the marked object, deriving authentication data from the captured characteristic data, comparing the authentication data with reference authentication data, and determining the authenticity of the marked object based upon the comparing.

In an embodiment, a method for determining the authenticity of a marked object includes providing a marked object for authentication, capturing an optical image of the marked object, performing optical characterization recognition of the captured optical image, deriving authentication data from the optical character recognition by extracting font information from the optical character recognition, comparing the authentication data with reference authentication data derived from statistical testing, including hypothesis testing of authentication data from a plurality of other marked objects, and determining the authenticity of the marked object from the comparing.

In an embodiment, a method for determining the provenance of a marked object includes providing the marked object, capturing an optical image of the marked object, performing optical characterization recognition of the captured optical image, deriving marking system data from the optical character recognition by extracting font Bezier curve information from the optical character recognition, comparing the marking data with reference marking system data derived from statistical testing of marking system data from a plurality of other marked objects, and determining the provenance of the marked object from the comparing.

In an embodiment, a method for determining the provenance of a marked object includes providing the marked object, capturing an optical image of the marked object, performing optical characterization recognition of the captured optical image, deriving marking system data from the optical character recognition by extracting font Bezier curve information from the optical character recognition, comparing the marking data with reference marking system data derived from statistical testing of marking system data from a plurality of other marked objects, determining the provenance of the marked object from the comparing, and authenticating the marked object by verifying its provenance.

In an embodiment, a system for determining the authenticity of a marked object includes a measurement system for capturing characteristic data from the marked object, storage for containing reference authentication data, a processor for deriving authentication data from the captured characteristic data, comparing the authentication data with the reference authentication data, and determining the authenticity of the marked object from the comparing; and an indicator of authenticity.

In an embodiment, an article including a computer program product having stored therein instructions that, if executed by a processing unit, configure the processing unit to: provide a marked object for authentication, capture characteristic data from the marked object, derive authentication data from the captured characteristic data, compare the authentication data with reference authentication data, and determine the authenticity of the marked object from the comparison.

In an embodiment, an article including a computer program product having stored therein instructions that, if executed by a processing unit, configure the processing unit to: provide a marked object for determining the origin of manufacture, capture characteristic data from the marked object, derive marking tool data from the captured characteristic data, compare the marking tool data with reference marking tool data, and determine the provenance of the marked object from the comparison.

In an embodiment, a method of identifying the origin of manufacture of a marked object includes capturing an image of the markings on the object, comparing the captured image with at least one reference authentication image in a database, wherein comparing includes determining the mathematical similarity or difference between the captured image and the at least one reference authentication image, and determining whether the marked object has the same origin of manufacture as an object associated with the reference authentication image based on this mathematical similarity or difference.

In an embodiment, a method for defining authentication data for a marked object includes providing a plurality of the marked objects belonging to a family, capturing a plurality of characteristic data from the plurality of marked objects, deriving a plurality of authentication data from the plurality of captured characteristic data, and analyzing the plurality of authentication data to determine one or more authentication parameters suitable for associating the plurality of marked objects with an additional marked object from the same family.

In an embodiment, a method for defining authentication parameters for a marked object of a first family includes providing a plurality of the marked objects of the first family, capturing a plurality of characteristic data from the plurality of marked objects of the first family, deriving a plurality of authentication data from the plurality of captured characteristic data, analyzing the plurality of authentication data to determine authentication parameters suitable for discriminating the plurality of marked objects of the first family from one or more pluralities of marked objects of additional families.

In an embodiment, a method for defining authentication parameters for marked objects includes providing a first plurality of marked objects of a first family, providing a second plurality of marked objects of a second family, capturing a plurality of characteristic data from the plurality of marked objects of the first and second families, deriving a plurality of authentication data from the plurality of captured characteristic data, analyzing the plurality of authentication data to determine authentication parameters suitable for discriminating the plurality of marked objects of the first family from the plurality of marked objects of the second family.

In an embodiment, a method for determining the provenance of a marked object includes providing the marked object for marking tool identification, capturing characteristic data from the marked object, deriving marking system data from the captured characteristic data, comparing the marking system data with reference marking system data, and determining the provenance of the marked object based upon the comparing.

BRIEF DESCRIPTION OF DRAWINGS

The present disclosure may be understood by reference to the following detailed description taken in conjunction with the drawings briefly described below. It is noted that, for purposes of illustrative clarity, certain elements in the drawings may not be drawn to scale.

FIG. 8 is set of images of two samples of a nominally identical marked object, marked by the same marking system, in accordance with an embodiment. The overlay of the edge-detected images of the two samples emphasizes the similarities attributed to the marking system.

FIG. 19 is a block diagram of an example tangible computer-readable medium 1900 having instructions 1902 stored thereon for controlling a processor.

DETAILED DESCRIPTION

Figure 1:
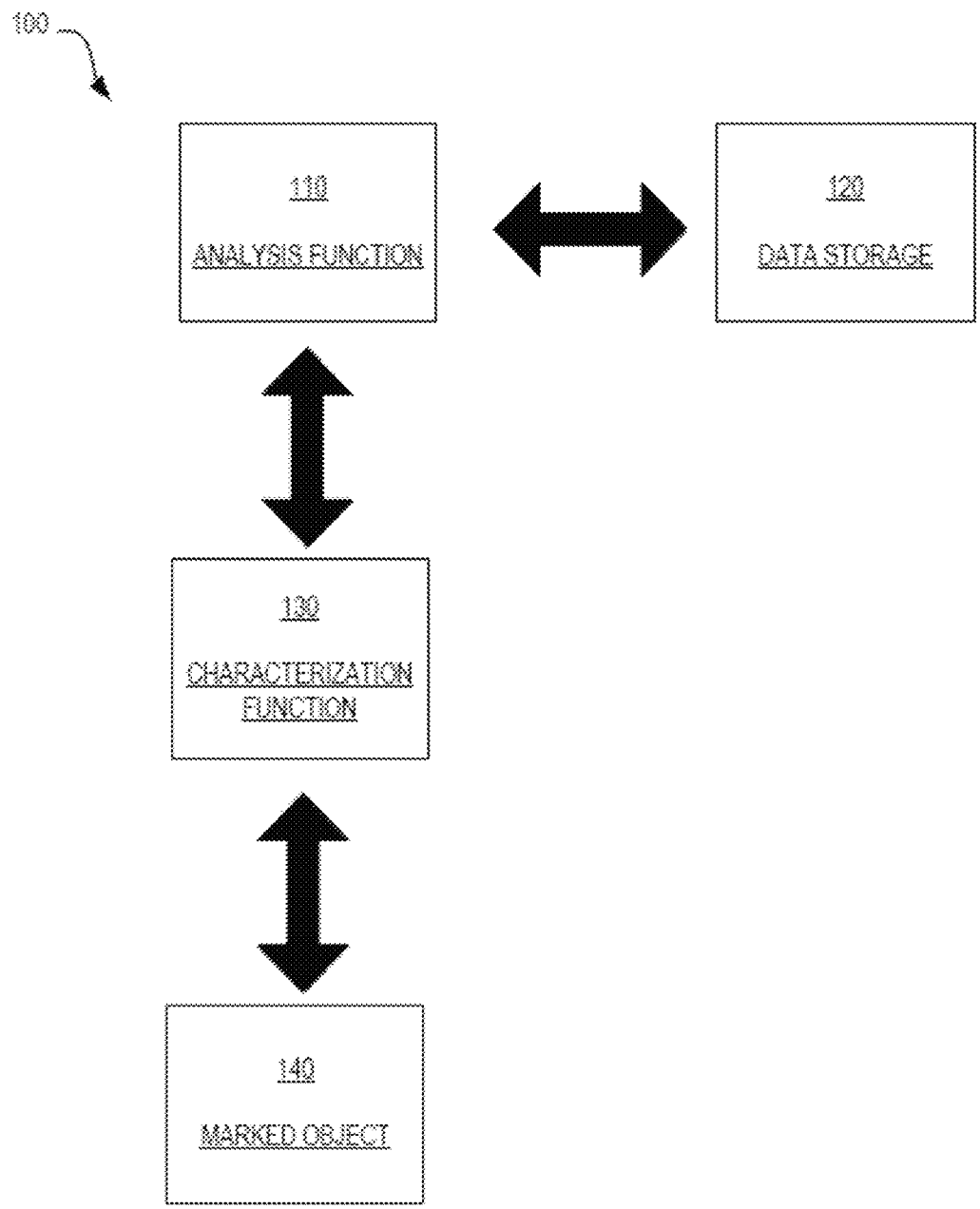
FIG. 1 is a simplified block diagram of an authentication system, in accordance with an embodiment.

The present invention has surprisingly found authentication does not require comparison to a historical record of the object of authentication to securely authenticate or determine provenance of the object of authentication. For example, features of an object of authentication may be compared against a historical record, e.g., a structured database, of the features of a family of nominally identical objects with known authenticity and/or provenance. Such authentication may proceed with high confidence by such a one-to-many comparison without requiring pre-existing characterization of the object of authentication.

As used herein, an "authentic" object may be understood to be associated with a known family of reference objects, regardless of provenance or genuine origin. An "authenticity score" may represent a Boolean value, a binned value, a probability, and the like, providing an estimate of the likelihood that the object is authentic, for example, whether there may be a match between the object and the family. "Authentication" is the process of matching one object to a related family of reference objects of authentication. The authenticity of the family may have been previously defined. A distinction should be understood between an object being genuine and "authentic." An authenticated object and an associated family may be either genuine or counterfeit. Authentication in this usage does not require access to any information beyond that which may be physically present with the object itself.

Information about the origin of an object and/or family may be considered the "provenance" of the object and/or family. This may include, for example, information on manufacturing of the object of authentication, e.g., a corresponding manufacturing time, place, manufacturer, lot, tool or process, or a determination of whether the object can be trusted. Thus, the process of establishing the provenance of an object may include both authentication and an association of the object and/or family to a set of information that may be exogenous to the objects.

As used herein, "font reconstruction" means a process of mathematically transforming characteristic data, e.g., images, of glyphs in a font and representing them in a mathematical form, e.g., a polynomial spline, a Bezier-curve spline, and the like. Authentication parameters may be extracted from such a mathematical transformation as a reconstructed font for use in authentication.

As used herein, "object of authentication" means any tangible substrate for which authentication is desired. For example, an object of authentication may be an article of manufacture. A "reference object of authentication" is other than the object of authentication and may be used for comparison in analyzing and authenticating the object of authentication. In various embodiments, the reference object of authentication may have a known authenticity, a known provenance, an unknown authenticity, or an unknown provenance.

As used herein, an "article of manufacture" means a man-made object, e.g., a molded part, a machined part, a 3D printed part, an embossed part, an extruded part, a forged part, and the like.

As used herein, "characteristic data" means raw or processed data obtained from a characterization module, for example, raw imaging data or formatted image data obtained from a camera, scanner, spectrometer, and the like. "Reference characteristic data" means authentication data corresponding to a reference object of authentication.

As used herein, an "electronic database" means a structured database used to store similar or different types of data, parameters, and the like. In some embodiments, an "electronic database" explicitly excludes information encoded in a trained neural network.

As used herein, "authentication data" means data or parameters derived by a mathematical transformation of characteristic data that is used to authenticate an object. "Reference authentication data" means authentication data corresponding to a reference object of authentication. As used herein, "authentication parameters" are descriptive parameters obtained by processing or analyzing the characteristic data that may be included in the authentication data. Authentication parameters may define or characterize an authentication function, such the parameters of a Bezier spline representation of an object, and the like.

As used herein, a "mark," e.g., on a man-made object, may include, for example, a font character, a glyph, a tooling or manufacturing mark, a printed mark, and the like. A mark may be made by an intentional marking tool, such as a printer or laser marking system. A mark may be made in the course of manufacturing, such as by a machining tool or a molding process.

The present invention represents a widely applicable and simplified system and method for authenticating or determining provenance and/or authenticity of marked objects. Other advantages of the current invention will be described in association with the described embodiments.

FIG. 1 shows a simplified block diagram of authentication system 100 which includes analysis function 110, data storage 120, characterization function 130 and marked object 140. Analysis function 110 may be connected with data storage 120 and with characterization function 130. Analysis function 110 may be electrically or otherwise connected to data storage locally such as memory or disk storage integrated with analysis function 110 or may be network connected storage. Analysis function 110 may be connected with characterization function 130 locally as integrated functionality of may use a communication interface such as Ethernet or USB. Analysis function 110 may be, for example, a fixed or portable computer system such as a laptop, personal computer ("PC"), smart phone or programmable logic controller ("PLC"). Analysis function 110 may actively control characterization function 130 or may passively receive characteristic data from characterization function 130.

Characterization function 130 may be any type of characterization suitable for the derivation of authentication and/or identifying information for marked object 140. For conventional light imaging technologies, characterization function 130 may be or be integrated with a camera, microscope, smart phone, scanner, Google Glass or other device. Other types of characterization may include fixed or portable instrumentation designed to provide such characterization.

A summary of example characterization methods are listed in Table 1. It should be understood that Table 1 is in no way exhaustive of possible characterization methods and that combinations of any of the listed methods are also possible. Any of the methods listed in Table 1 may be changed in order, replaced and/or combined with alternative methods known in the respective measurement art. For example, RGB color imaging may be substituted for CMYK color imaging.

TABLE 1

| Characterization Type | Sub-types |
| --- | --- |
| Light imaging | Color imaging, grayscale imaging, Spectroscopic imaging, IR/UV imaging, polarimetric imaging |
| Interferometric imaging | 1 D and 2 D optical profilometry, confocal microscopy interferometry |
| Fluorescence imaging | Phosphorescence intensity imaging, phosphorescence lifetime imaging, fluorescence lifetime imaging |
| X-ray | X-ray diffraction, X-ray scattering |
| Terahertz Scatterometry | |
| Mechanical profilometry | Atomic force microscopy |
| SEM | Electron contrast microscopy, SEM imaging, EDX |
| Non-linear optical characterization | $2^{nd}$-order NLO characterization, $3^{rd}$ order NLO characterization |
| Ultrasonic/acoustic imaging | Spatial contrast ultrasound, measurement of speed of sound in the object |
| Thermographic imaging | Thermal conductivity, heat capacity |

Analysis function 110 may perform automatic determination of identifying information of marked object 140 such as size, text description, and/or color in addition to deriving authentication information from characteristic data. Identifying information may be used to index the authentication information of marked object 140. The authentication and identifying information may be obtained using analysis methods including, but not limited to, those listed in TABLE 2.

TABLE 2

Analysis Methods

| | |
|---|---|
| statistical analysis | image deconvolution |
| principle component analysis | image correlation |
| roughness spectral analysis | edge extraction |
| reduced basis sets-wavelets | character recognition |
| neural network analysis | |

Authentication and/or identifying information produced by analysis function 110 may be stored into data storage 120 for future access. Data storage 120 may be a structured database such as a SQL database residing upon a local or networked server or may be "Cloud" or peer-based data storage. An authentication configuration associated with a marked object may include, but is not limited to, fields such as listed in TABLE 3. Certain data fields may be associated with object authentication and others may be associated with object provenance. The authentication data fields may be associated with the ability to relate an object to an object family during an authentication process such as process 300. The provenance data fields may be associated with the ability to relate the object family to a marking system and/or fabricator of origin.

TABLE 3

| Data Field Name | Description |
|---|---|
| ObjectName | Name, part number, serial number, and the like of the marked object |
| ObjectManufacturer | The manufacturer of the marked object |
| Date | The date of manufacture or authentication of the marked object |
| MarkingSystemID | The type, brand name, manufacturer, serial number, and the like of the marking system used to mark the object |
| AuthenticationFeatures | Authentication data derived from characterization of the marked object |
| AuthenticationAccuracy | A figure of merit determined from the repeated characterization and analysis of authentication features derived from characterization of one or more marked objects |

As detailed further herein, analysis function 110 may analyze characteristic data from characterization function 130 to determine a hierarchy of authentication information including, but not limited to, 1) characteristic data such as an unprocessed optical image; 2) authentication data including one or more authentication features such as formatting data of a character derived from optical character recognition (OCR) processing of the optical image of the marked object or a polynomial-spline descriptive representation of the character outline derived from the optical, e.g., the Bezier curves or kerning of a character derived from optical character recognition (OCR) processing of the optical image of a marked object and 3) an authentication value as a scalar metric or probability for authenticity or provenance such as a 99% chance of belonging to a specific family of objects, a 99% chance that the object does not belong to a specific family of objects, and the like.

Marked object 140 may be any object suitably marked so as to permit characterization and authentication by such systems and methods as described herein. A summary of example marking methods and associated marked objects are listed in Table 4. It should be understood that Table 4 is in no way exhaustive of possible marking methods or of types of marked objects and that combinations of any of the listed marking methods and objects are also possible.

TABLE 4

| Object | Marking Method |
|---|---|
| Paper products | Printing |
| Metal products | Stamping, forming, embossing, rolling patterns |
| Ceramic products, semiconductors | Metal depositing, patterning, exposing, etching, laser marking, ink jet marking, grain size distribution, grain shape distribution, grain composition distribution, dielectric depositing, doping, patterning, exposing, etching |
| Wood products | Carving, embossing, laser marking, thermal marking |
| Cloth | Dyeing, weaving, stitching |

Figure 2:
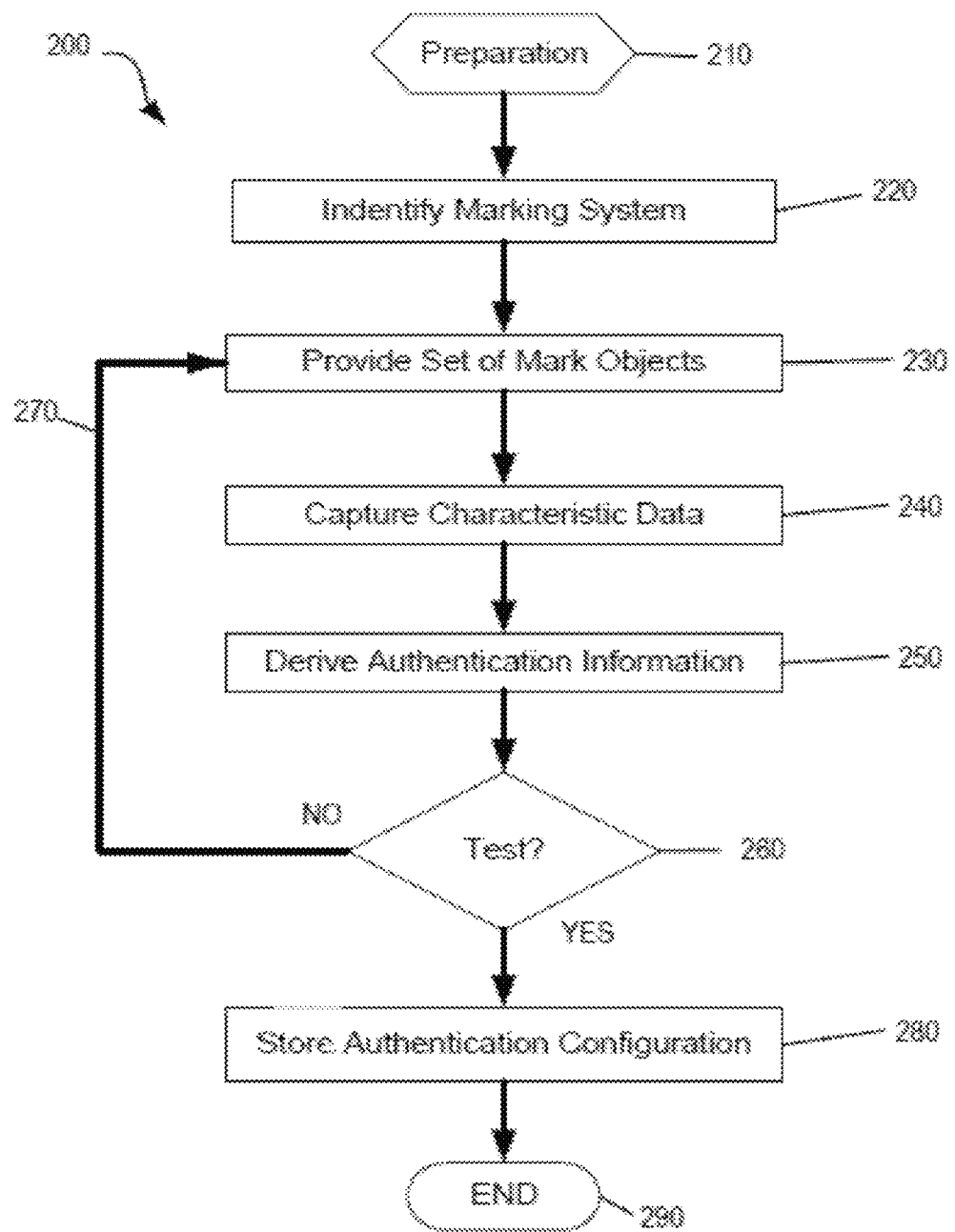
FIG. 2 is a flow chart of a process for defining authentication information for a family of marked objects, in accordance with an embodiment.

FIG. 2 is a flow chart of process 200 for defining reference authentication information for a family of marked objects. Process 200 may be used to derive any or all of the hierarchy of authentication information described in association with analysis function 110 of FIG. 1 above. Specifically, process 200 may be employed upon a collection of nominally identical marked objects to define therein one or more families of nominally identical marked objects, where a "family" represents a set of objects marked by the same marking system and displaying a shared set of authentication features and/or values. Additionally, one or more subfamilies may be defined within a family of marked objects where one or more discriminating features may exist. Reference authentication information may be created from characterization of a plurality of nominally identical reference objects and stored as any of the hierarchy of authentication information. Authentication information derived from characterization of an unauthenticated object may be compared against this reference authentication information to determine the authenticity of the object.

Features derived from characteristic data of reference objects useful for authentication may be sufficiently variable so as to provide the desired level of distinguishability or discrimination between different families of marked objects. However, the variability between the individual objects that are internal to a family may be ideally minimized. For example, when authenticating marked objects associated with multiple marking systems, the variability in features created by different marking systems may be high, but the variability of features of a single marking system may below. Thus, the process of characterizing the object may indirectly characterize the marking system that made the object. The marked object may be tracked back to this marking system even though the object may have never been characterized. This contrasts with authentication using a PUF where ideally variability may be high at the object level, and objects are not traceable back to their marking systems of origin. The low degree of variability of features within a family of marked objects permits discrimination of these features amongst all marking systems. The predictability of and limited access to the marking systems giving rise to the features may enable secure authentication. Laser marking and other marking technologies discussed herein may provide this appropriate degree of variability and sufficient common features.

The information derived from authentication data may include information (such as scalar values) associated with a single set of data. The information derived from authentication data may include information about the variability of the data within a family. Even within a family the marking may not be expected to be completely reproducible, and some characteristic variability may be expected in a given data set. A measure of the variability of features from object to object may be incorporated into the authentication data, which in turn may provide information for the determination of authentication values. Authentication may be based on the presence of the appropriate amount of variability or patterns of variability in a reference authentication data set. Additionally, unexpectedly low variation may also be an indication of a lack of authenticity.

The unique variability of laser marking systems provides a set of authentication features associated with a specific marked object, but which may represent the laser marking system that created it rather than completely unique to the object itself. This fingerprint may arise, for example, from inconsistencies in x-y tracking, spatial light distribution and laser intensity that may be inherent to a given laser marking system, yet which may be distinct from system to system, and may make it possible to identify the provenance of the object by correlating its marking features with those characteristic of the marking system that marked the object.

Variation may be evaluated by utilizing an existing pattern, such as an existing lot numbering system, and measuring the profile of the marks and the geometric shape of the overall pattern to establish a relationship between the mark and a specific laser marking system. Variations may be enhanced by programming the system to create specific patterns that enhance the ability to distinguish systems from one another, for example by instructing the system to draw a mark with features finer than its specified resolving range or at spacings that may challenge the tolerance of the x-y translation platform. The variability from system to system may be more easily identified, or the control within a system may be enhanced.

Process 200 initiates with step 210 wherein any necessary or optional setup and preparation steps may be performed. Setup and preparation operations may include the requisition of the appropriate number of marked objects, warm-up or calibration of a characterization system, determination of expected appropriate characterization system methods and data analysis methods, and the like. Once any desired preparatory operations are completed, process 200 may advance to step 220.

Marking system identification step 220 may include determination and recording of the marking method, e.g., laser scribing; the determination and recording of the make, model, serial number, manufacturer and owner of the marking system, e.g., LaserMark V12, S/N 123456789, produced in 2012 from Company XYZ, owned by Company ABC; or otherwise determining and recording of the source of the marked objects which may also derive from a known and trusted 3rd party rather than a manufacturer. This identifying information may be important in ascertaining the provenance of a subsequently measured marked object. It may further aid in the determination of authenticity, since the individual and deterministic features derived from each individual marking system and associated marked object may define the basis for the authentication data, algorithms and/or metrics.

Process 200 may include step 230 wherein a number of objects may either be marked using the marking system identified in step 220 or may be retrospectively verified as having been marked with the identified system or obtained from the identified source. Process 200 may be applied to existing marked objects subsequent to manufacture, for example, as long as the authenticity or provenance may be verified or otherwise indicated by some other method prior to inclusion of the existing marked objects into a database of reference authentication information. As used herein, "authenticity" may be generally applied to verifiably known counterfeit marked objects as well as marked objects of known provenance in general.

Process 200 may include step 240 wherein the marked objects are characterized with at least one characterization system and method such as described in association with FIG. 1 and TABLE 1. Step 240 may be performed at manufacture or at any future time as long as the authenticity or provenance of the marked objects may be verified or otherwise indicated. One or more characterization methods may also be combined to provide adequate or enhanced characteristic data and authentication information.

Process 200 may include step 250 wherein the captured characteristic data collected during step 240 may be analyzed and authentication information may be derived based upon methods appropriate to the type of marked object, the marking method, and the characterization method. Iteration of the analysis method may be desired for a new family of marked objects to provide stable and useful reference authentication information.

Derivation of authentication information follows from a chosen method of characterization such as optical imaging and a selection of a suitable method for the extraction of features from the characteristic data. For example, optical character recognition may be usefully combined with font reconstruction for authentication. Once an extraction method has been selected, a series of subprocesses may be undertaken to derive the authentication data. These subprocesses include, but are not limited to, extraction of features, analysis of extracted features, categorization of features, weighting and selection of features, classification of features and testing of the discrimination ability of features. These subprocesses may be performed in a wide variety of order and multiples of some subprocesses may be used. A detailed example of the derivation of reference authentication data for semiconductor chip packages follows in association with FIGS. 4-10.

Reference authentication information for families of semiconductor packages may be derived and authentication process evaluation may be performed by optical imaging of semiconductor chip packages followed by optical character recognition and font reconstruction processing to extract authentication features from the laser markings. A plurality of chip packages of known provenance and known association with more than one laser marking system may be first characterized by optical imaging. These optical images may next be converted to grayscale images and then custom font processed so that glyph feature information may be used for authentication. Custom font processing may be performed by application of software such as ClearScan (Adobe Systems Inc., San Jose, Calif.) to the grayscale images which may produce a type 1 postscript output, supplemented by case, kerning, font size/scaling and other character information.

Processing of this output may include one or more of: 1) analysis of the differences between similar glyphs marked by different laser marking systems, 2) the analysis of chip-to-chip variations within glyphs marked by the same laser marking system, 3) determination of a feature-vector mask that excludes feature dimensions that do not convey marking system information, 4) construction of an optimized system classifier from the inter- and intra-system statistics of glyph features, 5) proving of a clustering algorithm or linear classifier that correctly classifies every chip in the set of chips using a reduced set of features, 6) calculation of the resolving ability of the system classifier, and 7) evaluation of the performance of this classifier based on observed feature statistics.

For creation of a marking system classifier, a representative template may be created for each marking system to be classified by registering and averaging the characterization image data from all the chips in the collection, then de-noising and inverting the resultant image to generate a grayscale representation of the markings. Next a custom font may be created for the characters in each of the templates for the different families by digitizing the templates as a scannable document using a machine-vision character designation system, e.g. Clear Scan or Decapod (Decapod, available online at http://wiki.fluidproject.org/display/fluid/Decapod+ 0.7+Release). The glyphs may be represented as vector objects formatted as a type-1 CID font, which may also contain metadata about relative scaling and placement. The files for the OCR-resolved glyphs in the image and their formatting metadata may be extracted for later analysis and for import as a global (non-embedded) font using analysis tools such as FontForge (FontForge, available online at http://fontforge.github.io/) that may be used by other platforms.

In some embodiments, the template may be derived from images of the same object or objects, e.g., chip or chips, taken at multiple different exposure conditions. For example, images of a single chip may be taken using multiple different microscopes, multiple lighting brightness levels, multiple angles of illumination, and the like. For example, the template may be derived from images of a single chip in multiple conditions. The template may be derived from images of multiple chips under multiple conditions. The template may be derived from an image of a single chip that has been synthetically (computationally) altered to simulate multiple different image capture conditions.

The performance of the system-classifier may be measured by analysis of the differences between similar glyphs marked by different systems. This process may include converting the type-1 font files to a uniformly-sampled vector of polygon vertices for comparison, calculating a similarity measure of each glyph from the template in each family with respect to the same glyph from the templates of the other marking system associated families, and rank-ordering the glyphs by dissimilarity values between marking systems. Subsequently an initial determination of which glyphs marked on the chip package carry the most useful information for distinguishing between marking systems and therefore useful for authentication may be performed. This may be done, for example, by converting the type-1 font files to a format that that permits the polygon-vertex of glyphs from different marking systems to be compared using a similarity measure, then identifying those glyphs that demonstrate the greatest dissimilarity (lowest similarity measure) between marking systems. An example measure for this purpose may be the Jaccard distance between all the primitives in the glyph, but a variety of measures may be applied to optimize discrimination between marking systems and minimize susceptibility to noise. This analysis may also reveal which feature vectors in the glyph contain the most information useful for authentication.

Analysis of chip-to-chip variations within glyphs marked by the same marking system may include preprocessing of each chip image to facilitate OCR digitization and font reconstruction, rendering each chip image as an OCR document with embedded custom font, extracting the CID files of the glyphs for each chip's individual custom sub-fonts for every chip in each marking system family, converting the type-1 font files to a uniform vector representation for comparison and calculating the similarity measure of each glyph on every chip in each marking system family with respect to the same glyph from all glyphs in the marking system family.

The set of features of the candidate glyphs for marking system recognition may be filtered to determine which features show the least sensitivity to random uncontrolled variations within a given marking system's markings, which may permit distinguishing between the same glyph created by different marking systems. A custom font may be created for each individual chip in the family marked by each of the marking systems using the methods previously described. Glyphs showing the greatest dissimilarity may be analyzed to determine which features show the greatest correlation among different chips marked by the same marking system and may carry the most useful authentication information. Features that show the least correlation may represent noise. A good measure for this purpose may be the Pearson correlation, but a number of measures may be used.

Construction of an optimized system-classifier from the inter- and intra-marking system statistics of glyph features may include filtering the features in the representation of each glyph according to utility in discriminating between intra- and inter-marking system differences, performing a hard-cluster analysis on the sub-set of reduced glyph features for each marking system, and optimizing the classifier to this set of glyph features using methods suited to the classifier type. At this point, a representation has been derived of the sub-font of glyphs present in the marking system on the chips as imprinted by each of the marking systems, plus a sub-set of features that provide the greatest discrimination between the characters created by different marking systems. This may be a standard multi-objective optimization problem, which may be treated by a number of algorithms such as a distribution based cluster algorithm, for example, based on the feature distribution functions derived from the chip statistics, or a k-mean clustering algorithm that presumes a known number of clusters. Alternatively, a neural network may be used to train the classifier to identify the most relevant features for discrimination. An optimized classifier may be constructed from a plurality of characters by adaptively combining the separate classification processes of a plurality of weakly discriminating characters to "boost" the classifier discrimination, e.g., using "AdaBoost" method by Freund and Schapire.

Calculation of the performance of the laser marking system classifier may include performing an internal evaluation of the classifier on all the chips within a first family or collection using the glyph features used to train the classifier, digitizing the laser markings from a second family or collection of chips and generate their glyph features using the methods discussed above, and performing an external evaluation of the classifier on all the chips in the second family or collection using the equivalent glyph feature. The internal evaluation may be performed by applying the classifier to the (digitized) laser training markings, and using the statistical distribution of points in the vector space generated by the classifier the characterize the resolution. A standard measure for characterizing the resolving power of a classifier such as the Davies-Bouldin index may be used. If this value is sufficiently high, it may be concluded that the classifier has high descriptive validity.

The external evaluation may be performed by first digitizing the laser markings on the second family or collection of chips using the procedure described above. The classifier may be applied to the glyph data for all the chips and the number of false positives and false negatives recorded. A standard measure for characterizing the resolving power of the classifier on the external data, such as the Fowlkes-Mallows index may be used. If the difference between this index and the internal index is small (i.e., the Fowlkes-Mallows index is also high), then it may be concluded that the classifier has high prescriptive validity as well.

A similar procedure may be applied to what may be described above for distinguishing between characters produced by different marking systems to the problem of distinguishing the formatting characteristics of each marking system. The formatting data—kerning, line spacing, in-line glyph placement—also may be captured and extracted using commercial OCR software. The relative positioning of a glyph in a character box may be contained in the metadata provided by ClearScan as "hints," but rather than working with the ClearScan metadata to analyze the global layout of the markings on a chip, the labeled fonts may be exported for each marking system to other OCR platforms, e.g., FineReader (ABBYY, Milpitas, Calif.).

The system-markings templates created for each marking system may be rendered, then the formatting data extracted. This data may be treated as another feature set that may be distinct from the font features, and also may be represented in abstract vector form. The formatting vectors of all of the chips marked by the marking systems may be analyzed for similarities within a family or collection and dissimilarities between families or collections by the same procedures discussed above for glyphs. Because of the more discretized nature of a formatting data vector versus a glyph vector object, a measure such as the Tanimoto coefficient may be used for this purpose, although a number of measures may be used. The resolving power of the matrix may be measured before and after this addition to quantify the improvement made by the additional dimensionality.

The resolving power ("R") of a given feature may be defined as the ratio of the specified control capability (dControl) of the production of a feature and the resolving capability (dAnalysis) of a characterization method used to characterize the feature: R=dControl/dAnalysis. The resolving power relates both to the level of variability in a feature as well as the ability of that feature to be used to discriminate amongst or within a family of marked objects.

For example, a lithographic process may have an alignment capability of 10 nm, and characterization by SEM may have a resolution of 1 nm, therefore the resolving power may be 10. This number may be low relative to the number of families of marked objects for which discrimination and unique identification may be desired. This problem of low R for a given characterization method may be partially alleviated by deriving multiple features from the characteristic data that result from the same manufacturing process, which may enhance the resolving capability as long as the features are decoupled from each other. For example, in analysis of laser marked objects, one may expect the laser spot size to be decoupled from the x-axis translation distance between characters, which in turn may be completely decoupled from the time the laser dwells in a location at the start of a character. These three different features may be characterized simultaneously to provide a resolving power that may be the product of each individual element: $R=R_1*R_2*R_3$.

Some features may be partially decoupled, for example, the x-axis translation on a stage may be independent from the y-axis translation, or may not, and for such elements the true R may be empirically determined. For the derivation of the most robust authentication information, the highest possible theoretical resolving power may be targeted, and because of the multiplicative power of resolving unrelated elements, a rich feature space may be desirable to obtain the best results. The example laser mark identification system described herein may be based on optical imaging because of the richness of this space: the product of many small details such as line width, pooling, stroke patterns, and the like may enable improved resolving power when combined. The addition of other imaging modalities such as interferometry and SEM may offer further capability.

In various embodiments, the present invention may be used to analyze an intentionally marked object, such as an object that has been marked by a laser. Surprisingly and unexpectedly, sufficient information resides in the two-dimensional outlines that result from marking to successfully distinguished marked parts. This result was unexpected because laser marking systems may be used to "spoof" existing marks. Such systems are specifically designed with 25 or more different adjustable parametersso output can be tuned to mimic that from other equipment. However, the present methods may distinguish marking by two different tools, even when a first tool is professionally tuned to mimic the output from a second tool.

The mathematical framework described above may be highly modular—any feature that may be determined at a later stage to be useful may be added as a dimension into the authentication information without any significant changes to the framework itself. The improvements in resolving power associated with this new feature may be automatically calculated. The framework may allow for rapid evaluation of potential improvements as more data may be collected.

Process 200 may include to step 260 where a determination may be made of the suitability that the extracted features and derived authentication information may be appropriate for the authentication of the targeted marked object family. Determination of suitability may include cross-evaluation of the newly derived authentication data against the authentication data one or more existing families to assess distinguishability. For example, the calculation of a discrimination metric and comparison of the discrimination metric against a threshold may include, for example a value of 99%, to determine suitability. Such a threshold may be set as a goal or may be correspond to the number of available marked objects.

Since authentication may correspond to the interaction of the marking system and the marked object, a metric for authentication may include a value or threshold for discrimination between either/both marking systems or/and marked objects. Determination of a desired level of confidence of authentication may use a sufficient portion of a family of marked object to establish a level of confidence. However, determination of the desired level of confidence may proceed without characterization and analysis of 100% of a family of marked objects associated with a specific marking system.

Step 260 may include testing or enhancing the robustness of the authentication data by one or more of: 1) sampling nominally identical marked objects from the same marking system over a period of time (e.g., one week, one year, and the like), and evaluating suitability; 2) sampling similarly marked objects from a plurality of sources; 3) establishing minimum sample sizes and sampling frequencies desired to create the reference authentication data for that family of marked objects; 4) revising the derived authentication data over time to include only those features of the highest resolving power and most unspoofable features; 5) automatic inclusion of new families of marked objects and re-derivation of new authentication information for one or more families to improve discrimination and authenticity determination; 6) characterization of similar objects by different marking systems; 7) characterization and analysis of counterfeit objects and 8) characterization of different objects marked by the same marking system.

Process 200 may include step 280 wherein analysis parameters and other information may be stored for future access as an authentication configuration. If the authentication suitability threshold score and analysis determination ability is judged insufficient, process 200 may return to step 230 via route 275 and further objects may either be marked or added to the set to be analyzed. Optionally, process 200 may return to any of steps 240, 250 and 260 wherein alternative characterization and/or analysis methods may be applied to the marked objects.

Process 200 may terminates with end step 290 following completion of authentication thresholding and analysis of determination ability. Step 290 may include actions such as operator training, system configuration for automatic authentication, data archiving and/or documenting authentication procedures.

Figure 3:
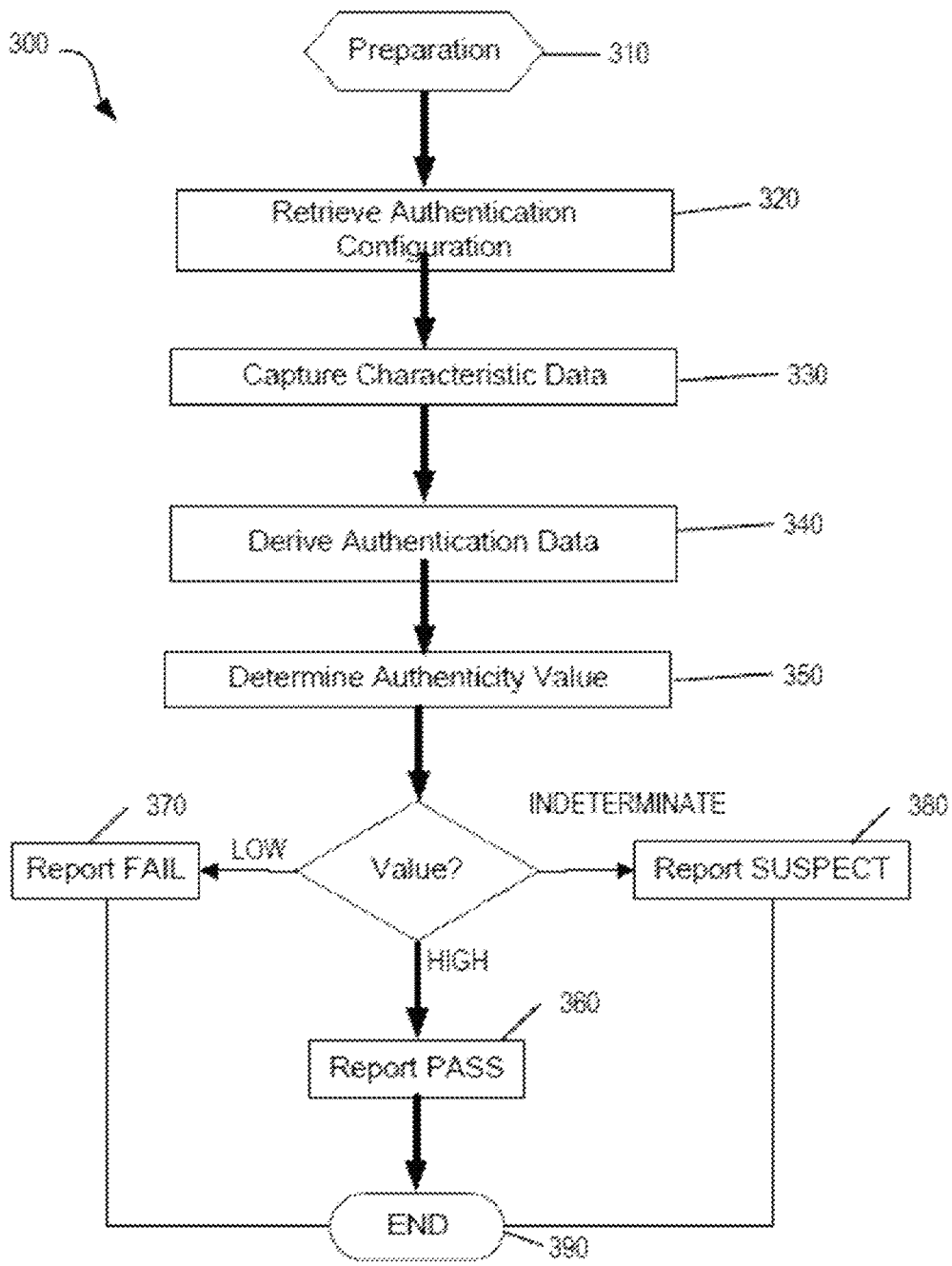
FIG. 3 is a flow chart of a process for authenticating a marked object, in accordance with an embodiment.

FIG. 3 is a flow chart of process 300 for authenticating a marked object. Process 300 may include step 310 wherein any necessary or optional setup and preparation steps may be performed. Setup and preparation operations may include the proper determination of a marked object, and warm-up or calibration of a characterization system. Process 300 may include step 320 wherein the appropriate authentication configuration may be retrieved from data storage such as a secure web server. The authentication configuration may include the details of the characterization system and methods used in subsequent steps. Example authentication configuration data fields are shown in TABLE 3. Process 300 may include step 330 wherein the marked object may be characterized. Characterization of the marked object may be done by any method discussed herein such as discussed in association with TABLE 1.

Process 300 may include step 340 wherein the captured characteristic data may be analyzed to derive the authentication data. Analysis methods and procedures described herein in association with TABLE 2 may follow a prescriptive method relayed in the authentication configuration and may include processing similar to analyses associated with step 250 of process 200. Process 300 may include step 350 wherein the current authentication data may be compared to the retrieved authentication data to determine a match value or probability of being authentic. The comparison method may be relayed in the authentication configuration and may include processing similar to analyses associated with step 250 of process 200.

Based upon the value of the authenticity score, process 300 may report an authentication PASS indication in step 360, an authentication FAIL indication in step 370 or an authentication SUSPECT indication in step 380. Additionally or optionally, process 300 may report a raw probability value or other finer or coarser indication ranges of authentication such as 5% or 99.7% chance of authenticity. In an authentication system having a user interface, the indication could be, for example, a colored indication with red for fail and green for pass. Process 300 may end with step 390 following indication of authenticity.

Characteristic data useful for authentication system 100 such as described in association with FIGS. 1, 2 and 3 may be provided by optical image capture of marked objects. FIGS. 4-9 present examples of characteristic data that may be processed by the steps of processes such as 200 and 300 to define authentication information and provide for authentication of marked objects, respectively. FIGS. 4-9 specifically exemplify the characterization of marked semiconductor chip packages and the authentication and/or determination of provenance of marked semiconductor chip packages.

Figure 4:
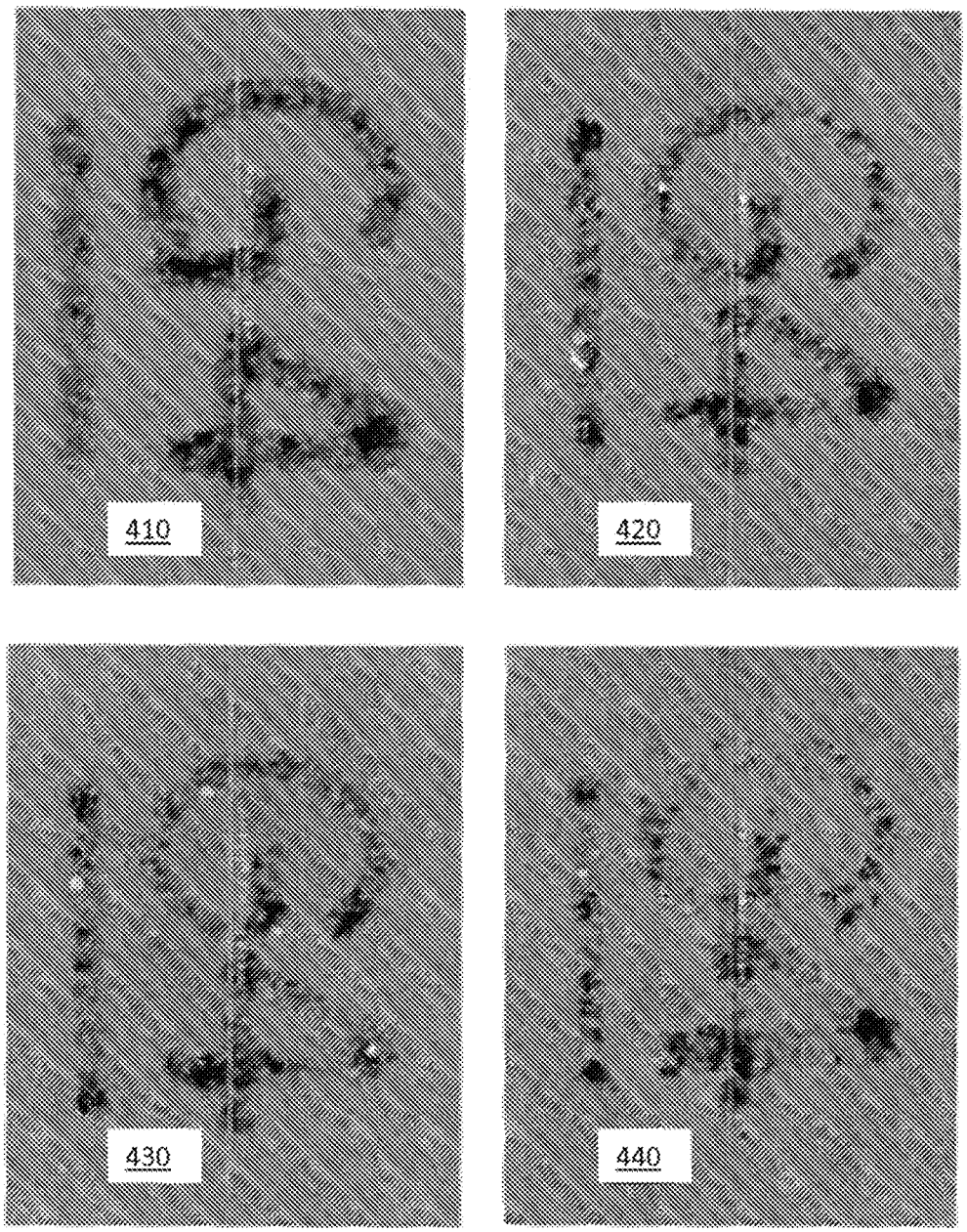
FIG. 4 is a composite of images of four marked objects showing similarities and differences between multiple samples of a nominally identical marked object marked with three different marking systems, in accordance with an embodiment.

For example, FIG. 4 includes a composite of images 410, 420, 430 and 440 of four marked semiconductor chip packages showing feature similarities and differences between multiple samples of nominally identical marked semiconductor chip packages marked with three different laser marking systems. Images 420 and 430 are derived from semiconductor chip packages marked by the same laser marking system and images 410 and 440 are derived from semiconductor chip packages each marked by additional different laser marking systems. The four marked semiconductor chip packages of FIG. 4 constitute a collection of nominally identical marked objects which may be subdivided into three families of marked objects associated by marking system.

The consistency of features between the markings for images 420 and 430 may be visually observed and inconsistencies of features between images 410, 440 and the pair 420 and 430 may also be visually observed. Observable features within these images are listed, but not limited to, those enumerated in TABLE 5.

TABLE 5

| | |
|---|---|
| Width of a single line | Consistency of the traces |
| Depth of a single line | Shape of the "G" |
| Spacing between the characters | Unmarked area inside the "4" |
| Pattern of depths within one character | Spacing in between individual laser marks |
| Depth of individual laser marks | Radius of individual laser marks |
| Frequency-dependent amplitude of laser marks | Depth profile of a single line |

Any of these individual features and associations amongst any one or more of these features may be used to define authentication data and one of more authentication features useful for comparison between related marked objects such as any two semiconductor chip packages within a family and between genuine and counterfeit marked objects which may represent different object families.

In detail, the analysis of the optical image characteristic data of FIG. 4 may provide a set of authentication data derived from optical character recognition and font analysis. Specific features derived from the authentication data may then be used as authentication features for determining relationships among nominally identical marked semiconductor chip packages permitting the establishment of association with and discrimination amongst other families of similar marked semiconductor chip packages in a collection.

For example, the width of a single line that defines the letter 'G' may constitute a first scalar authentication feature in a set of authentication features associated with a family of marked semiconductor chip packages. Additionally, the width of the line that defines the number '4' may constitute a second scalar authentication feature, and the width of the line beneath both the 'G' and the '4' may constitute a third scalar authentication feature associated with a family of marked semiconductor chip packages. More authentication features may be defined based on other authentication data derived from the characteristic data of the marked semiconductor chip packages in the collection. For example, the x-y locations or rotation of the 'G' and '4' characters relative to a defined fiducial or to each other may define a vector or matrix authentication feature for a family of marked semiconductor chip packages. Character grayscale values; data defining the Bezier curve associated with a font fit to the character; kerning between characters; size of the font and other authentication data may define additional authentication features.

Authentication data may include data dimensions related to the variation of the authentication features used to create the reference authentication data, so that calculations of likelihood of authentication between an unauthenticated marked object and the family of marked objects referred to by the reference authentication data may be made. Some authentication data and/or features may not be useful for permitting the establishment of association with and discrimination amongst other families of similar marked objects in a collection. Excessive or minimal variability in an authentication feature may inhibit definition of reference authentication data for a family since the feature may not permit grouping of or discrimination amongst families of marked objects in a collection.

Figure 5:
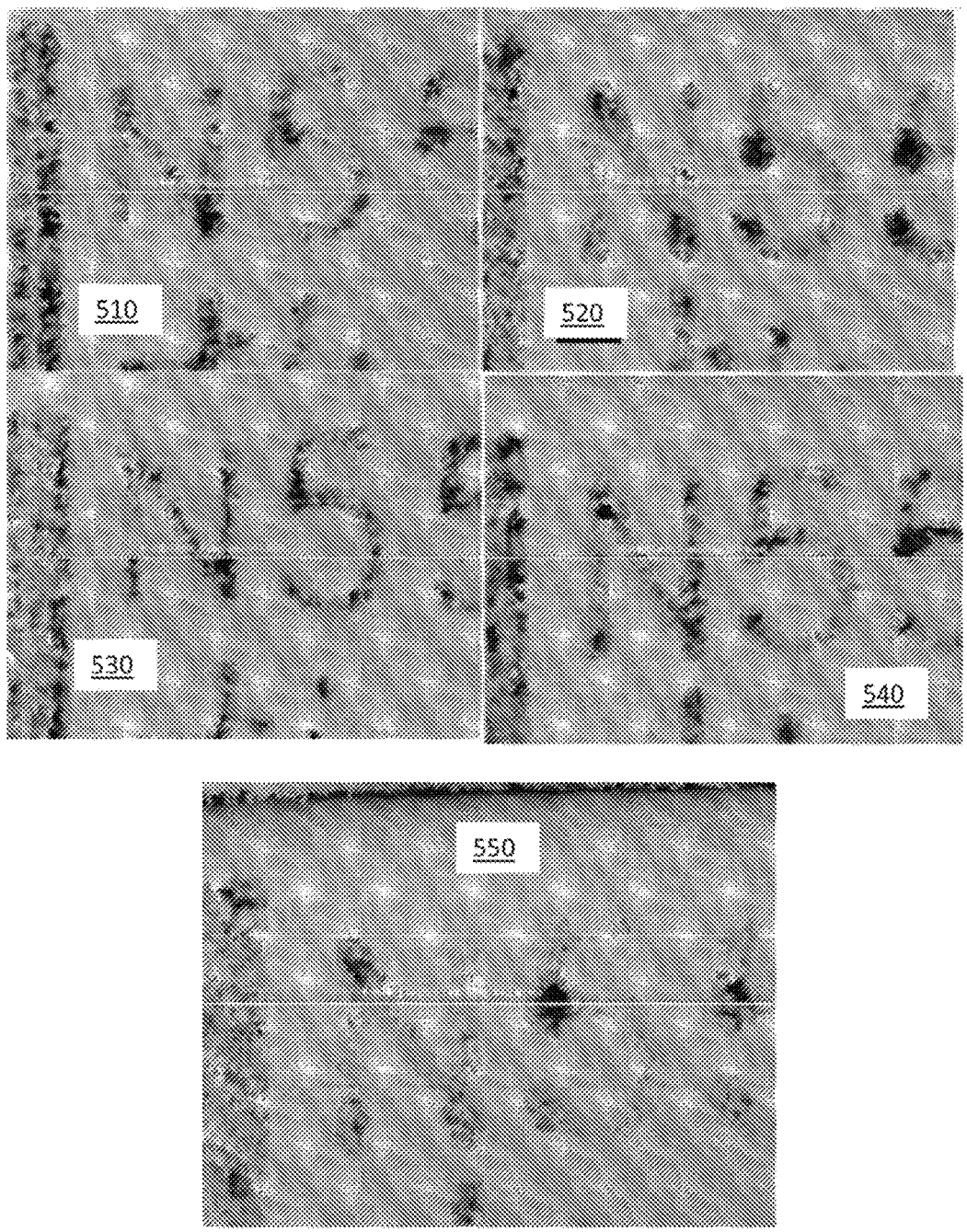
FIG. 5 is a composite of images of five marked objects showing similarities and differences between multiple samples of a nominally identical marked object marked with four different marking systems, in accordance with an embodiment.

FIG. 5 includes a composite of images 510, 520, 530, 540 and 550 of five marked semiconductor chip packages showing feature similarities and differences between multiple samples of nominally identical semiconductor chip packages marked with four different marking systems. Images 520 and 550 are derived from nominally identical semiconductor chip packages marked by the same laser marking system. The five marked semiconductor chip packages of FIG. 5 constitute a collection of nominally identical marked objects which may be subdivided into four families of marked objects associated by marking system.

Similar to the images of FIG. 4, consistencies and/or inconsistencies of features within these images may be visually observed and may be used to define authentication data and/or features for the families of semiconductor chip packages. Observable features in addition to those listed in TABLE 5 are listed, but not limited to, those enumerated in TABLE 6.

TABLE 6

| Width of the lines | Consistency in the letter (for example may be the "5" complete?) |
| Horizontal spacing between characters | Vertical spacing between characters |
| Angles of the lines relative to each other | Consistency of depth |

Such consistencies and/or inconsistencies of features may be analyzed mathematically and reduced, such as by steps 250 and 260 of process 200, into a number of authentication features useful for determining authentication. Mathematical analysis may include determination of reduced basis sets, image deconvolution, image correlation, edge extraction, determination of fitting parameters designed to measure specific aspects of the image and/or application of mathematical analysis techniques such as principal component analysis or other analyses listed herein.

Figure 6:
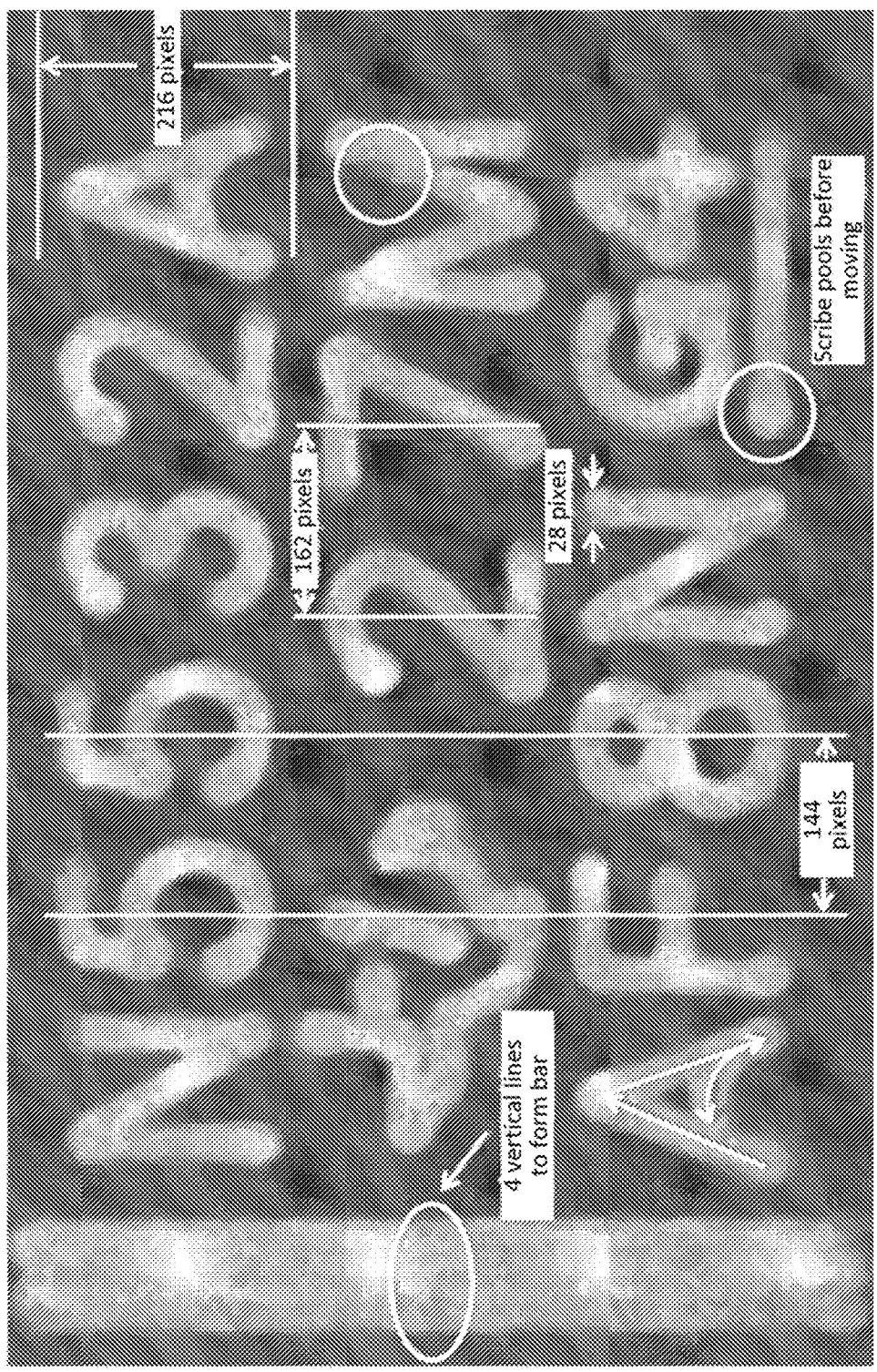
FIG. 6 is an image of a marked object showing relationships between markings that are useful for authentication of a family of marked objects, in accordance with an embodiment.

FIG. 6 is an image of a marked semiconductor chip package showing relationships between markings that may provide authentication features capable of uniquely identifying a family of marked semiconductor chip packages. The origin and authenticity of a marked semiconductor chip package may be determined by characterization of the markings of each semiconductor chip package. The marking may provide a unique set of authentication data and features that were integrated with the semiconductor chip package by laser inscription on each semiconductor chip package. Furthermore, the authentication data and features may be uniquely associated with a specific fabrication facility and laser marking system controlled by that fabrication facility. The control of the authenticity may reside in the control of the laser marking system, and not in the supply chain management of millions of different products. In the case of semiconductor fabrication facilities, security may be often tightly controlled and therefore may not permit easy unauthorized access. Decommissioning of laser marking systems secures the authenticity of old-stock parts since the marking system may not be readily duplicated.

Figure 7:
FIG. 7 is set of images of two samples of a nominally identical marked object, marked by different marking systems, in accordance with an embodiment. The overlay of the edge-detected images of the two samples emphasizes the differences attributed to the marking systems.

FIG. 7 is set of images 720 and 730 of two samples of nominally identical marked semiconductor chip packages, marked by different systems. The overlay 710 of the edge-detected images of the two samples emphasizes the feature similarities and differences attributed to the marking systems. The discussion of FIG. 7 references the features of the exemplary characteristic data from the images of FIGS. 4, 5, and 6 above.

The laser markings may carry unique features at two different scales. The first scale may be uncontrolled variations in the uniformity and intensity of the laser marks created by nonlinear interactions between the laser and the beam delivery system, which may be identified by microscopic inspection at the level of the character and character elements. These features may be evident, for example, in the differences in features of the "N" in the upper left of both images 720 and 730 and readily observed in the edge-detected overlay 710.

The second scale may be unintended variations in the presentation of the characters and symbols with respect to each other and the physical chip package, which may result from interactions between the graphics software, control of the beam delivery head, and the time characteristics of the shuttering of the beam. These features may be evident, for example, in the differences in position and kerning of the majority of the characters and logo of both images 720 and 730 and may be readily observed in the edge-detected overlay 710. Any of these features may be used as authentication features if deemed suitable by analysis, such as discussed in association with process 200 and step 250.

FIG. 8 is set of images 820 and 830 and an overlay 810 of two samples of nominally identical marked semiconductor chip packages, marked by the same marking system. In contrast to overlay image 710, overlay 810 clearly indicates the feature similarities in position and kerning of the majority of the characters and logo. Comparing the images of FIGS. 7 and 8, it may be evident that kerning of one or more individual characters may be used as an authentication feature that may have a high degree of similarity within a family of objects, but a high degree of difference between families of marked objects.

Figure 9:
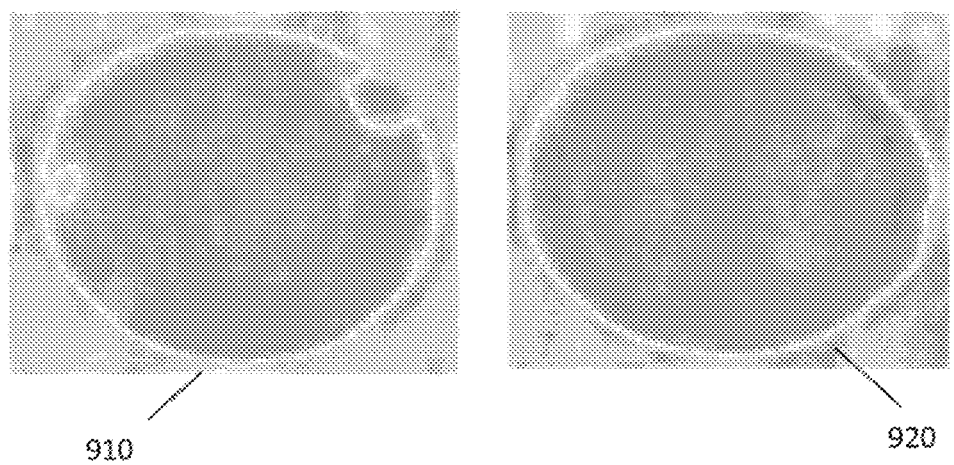
FIG. 9 is set of topographic images of two samples of a nominally identical marked object, marked by different marking systems, in accordance with an embodiment. The images indicate the discrimination possible between supposed identical marks attributed to differences between marking systems.

FIG. 9 is a set of high resolution topographic images of nominally identical features from two samples of a nominally identical marked object, marked by different marking systems. The images indicate the feature discrimination that may be possible between supposed identical marks attributed to differences between marking systems at resolutions higher than that provided by the character recognition processing detailed above.

Figure 10:
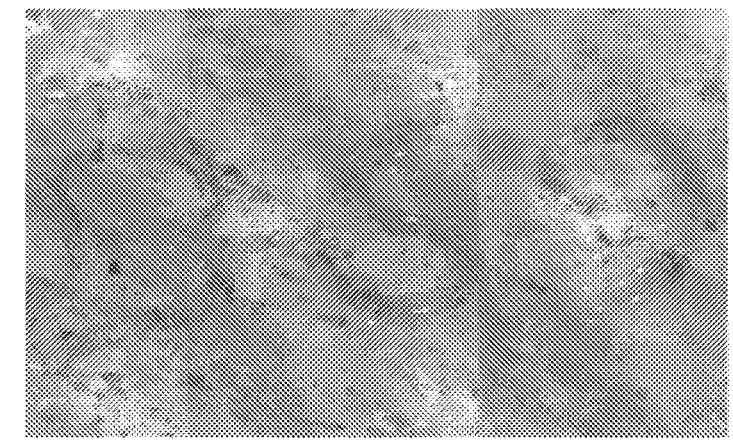
FIG. 10 is an image of a pharmaceutical tablet embossed or cast with identifying numbers which may be used to authenticate the manufacture of the tablet, in accordance with an embodiment.

FIG. 10 is an image of a pharmaceutical tablet 1000 embossed or cast with number characters that may be used to identify and authenticate the manufacture of the tablet. The number characters on the pharmaceutical tablet are commonly used for visual recognition and identification of the tablet. By themselves, the number characters are not well suited for authentication since the characters may be easily spoofed by a counterfeiter. However, similar to the authentication of the semiconductor chip packages discussed above, the imaging methods and systems discussed herein above may be used upon the cast, molded or printed tablet number characters to provide authentication or to determine provenance. The method of this invention may thus be productively applied to a variety of manufacturing processes which produce features which are traceable back to the marking system of origin, and the specific example applications of laser marking, molding, casting, printing, and the like are not meant to limit the scope of the invention.

Using the authentication methods and systems defined herein, the tablet may also be authenticated at any point along the distribution path from production and bulk packaging to the pharmacist and users. Additionally, the tablet authentication may proceed without changes to tablet manufacturing processes. Such tablet authentication may be performed by reading the tablet characters using a simple USB microscope or macro lens attachment for a smart phone. Image capture of a tablet may be done by any participant in the supply chain. Analysis of the image data and comparison of the tablet authentication data with reference authentication data stored in the cloud may provide an indication of a match or of a lack thereof.

The markings upon pharmaceuticals may include color or particle size distributions that may be sufficiently difficult to spoof and may be characterized by image processing or other techniques discussed herein. For example, the inclusion of pigment particles in pharmaceuticals is common practice. The FDA maintains a large list of pigments and dyes that may be included in drugs while exempt from batch certification, as well as dyes that are approved for drugs but subject to batch inspection. Example pigments and dyes suitable for use in this solution include: Iron oxide (rust), Carmine (red), Canthaxanthin (red-orange), Titanium dioxide (white), D&C Green No. 5, FD&C Blue No. 2, FD&C Yellow No. 6, and the like.

In the manufacture of a pharmaceutical tablet, at least one and often more than one of the above colored components may be mixed in with the drug as part of the pill formulation. The identity of the components, as well as the size of the particles, may be rotated on a regular basis, where each new batch may contain a distinct "code" including, for example, one or more of: the particle density (e.g., particles per square millimeter of surface of the pill); the particle size; the ratio of each particle with respect to the other; and the like. The particles may desirably be obtained in sizes not conventionally available on the open market, in order to discourage spoofing. Image analysis of these colored particles may provide authentication data for the tablet. Features related to the colored particles and to the marking and molding of a tablet may include relative particle positions, particle tilts, obscuration/embedment, and the like. Similarly, tablet grain size, texture and/or surface roughness related to mixing and pressing operations may provide features suitable for authentication using the system and methods of described herein by associating any tablet with specific production systems of known/controlled provenance.

Figure 11:
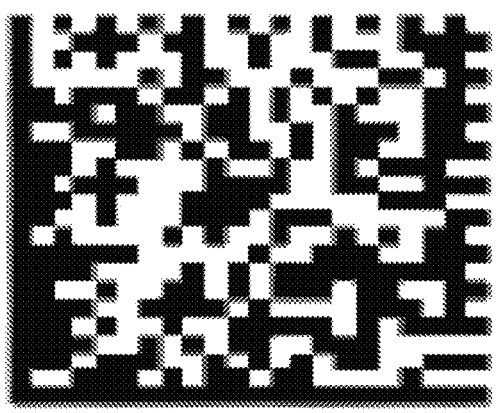
FIG. 11 is an image of product markings including text and a 2D barcode. Authentication of an object marked in such a way may be done by analysis of the characteristics of the markings and their relationships to other marks on the same object rather than relying only upon the barcode and/or text itself, in accordance with an embodiment.

FIG. 11 is an image of product markings 1100 including text and a 2D barcode. Authentication of an object marked in such a way may be done by analysis of the marking features and the relationships between marks on the same object rather than relying only upon the barcode or text itself. In FIG. 11, the text has be purposely skewed and the font size of the top line adjusted to emphasize the ability to apply the OCR-based authentication systems and methods described herein. The detection of this skewing and font size changes followed by comparison with the appropriate authentication reference data may be used to authenticate for example a pharmaceutical package or consumer product. In another embodiment, the details of the printing of the bar code, including such features as the rounding of corners, may be captured using the processes described herein and may be used to authenticate an object. In this use, although the bar code may be designed to encode information digitally, analog features may be extracted to ensure authenticity.

Figure 12:
FIG. 12 is a set of images of the front and back surfaces of a smart phone battery as a typical marked consumer object including text, 2D barcode and other symbols. Authentication of an object marked with such information may be done by analysis as described in association with FIG. 11, in accordance with an embodiment.

FIG. 12 is a set of images of the front surface 1210 and back surface 1220 of a smart phone battery 1200 as a typical marked consumer good including text, 2D barcode and other symbols. Authentication of an objected marked with such information may be done by analysis as described in association with FIG. 11.

Figure 13:
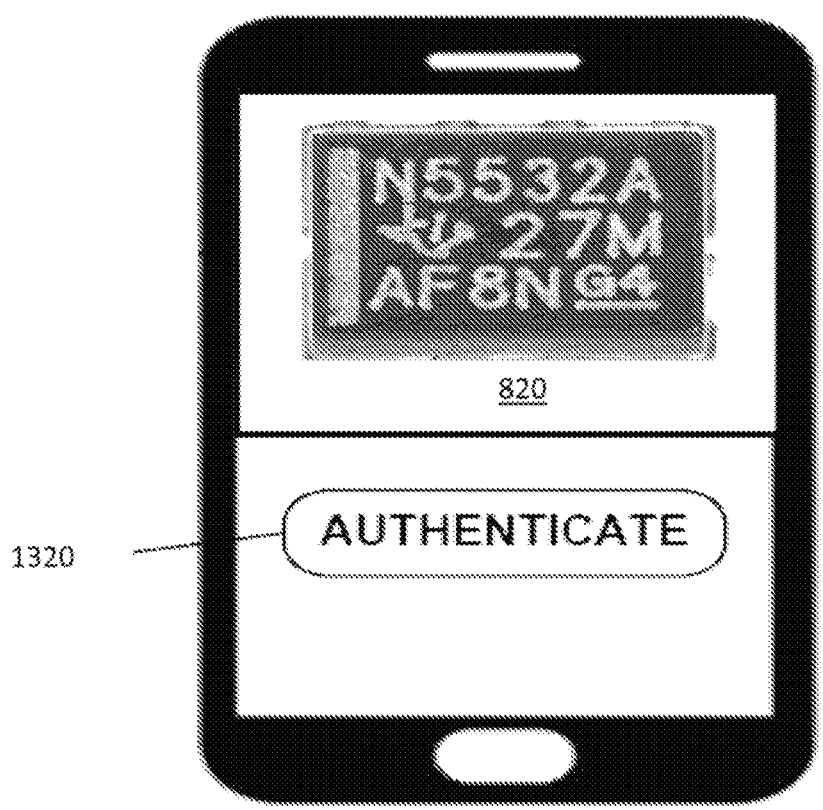
FIG. 13 is a conceptual image of a user interface for an authentication application for a smart phone, in accordance with an embodiment.

FIG. 13 is a conceptual image 1300 of a user interface 1310 for incorporation of an authentication application, based upon the systems and methods described herein, into a smart phone. An authentication application may form a stand-alone self-contained authentication system or may be realized as a distributed system with characterization by optical imaging provided at a first location (smart phone camera) and analysis and determination of authenticity performed at a second location such at a remote server. The remote server may supply a reply to the smart phone application indicating if the item imaged may be genuine, counterfeit or indeterminate. The user interface presents an image of an object to be authenticated, e.g., image 820, and a control, such as button 1320 for prompting authentication.

Figure 14:
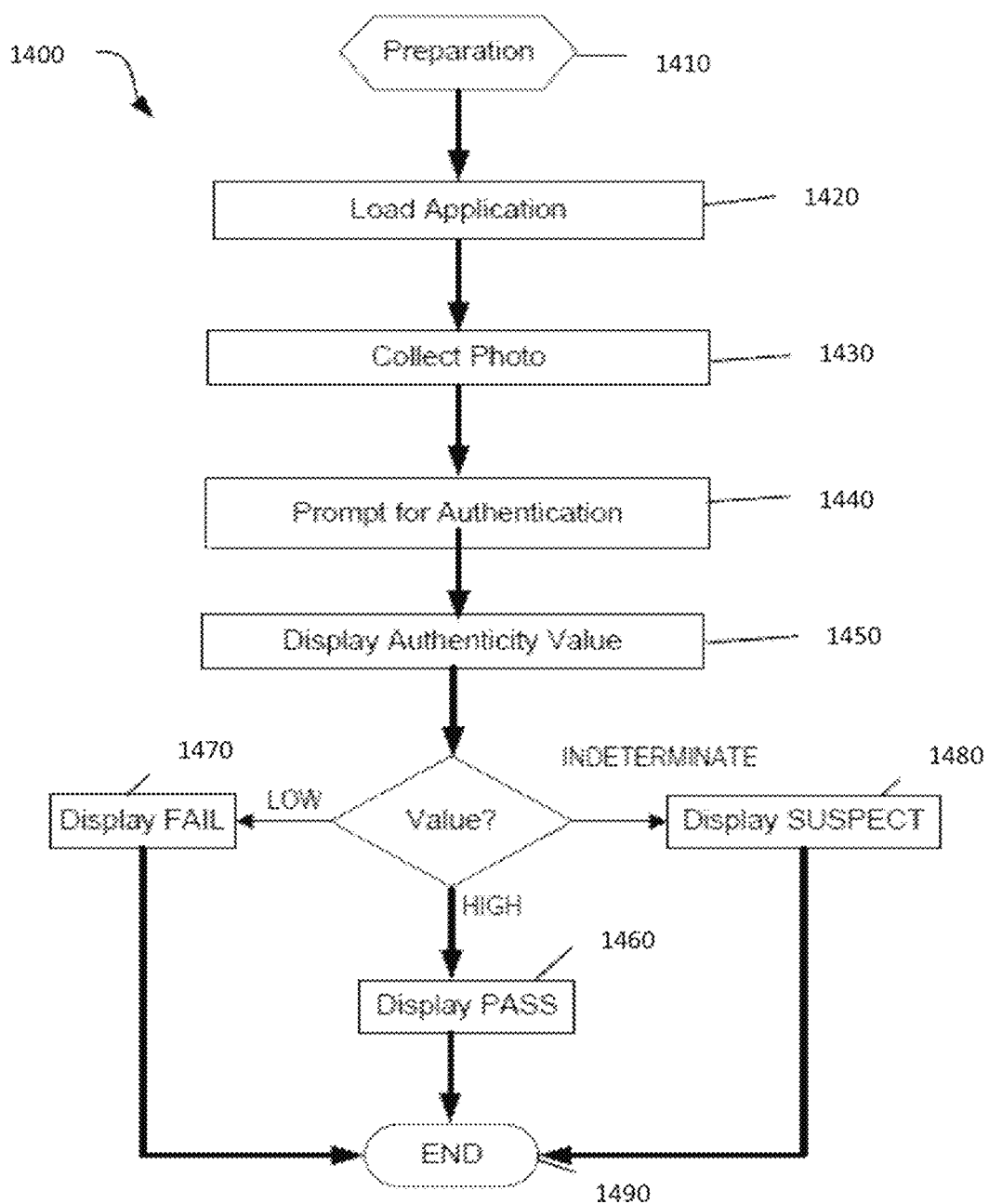
FIG. 14 is a flow chart of a process for authenticating a marked object using an authentication application such as shown in FIG. 13, in accordance with an embodiment.

FIG. 14 is a flow chart of process 1400 for authenticating a marked object associated with a marking system using an authentication application such as shown in FIG. 13. Process 1400 initiates with step 1410 wherein any necessary or optional setup and preparation steps may be performed. Setup and preparation operations may include the proper identification of a marked object or staging of the item to permit characteristic data capture via imaging as described herein. Process 1400 may include step 1420 wherein the authentication application may be loaded into the processor and memory of a device such as the smart phone of FIG. 13. Once loaded, the application may display a user interface such as in FIG. 13 with an image and button 1320. Process 1400 may include step 1430 where an image may be captured and displayed such as shown.

The image may then be reviewed and deemed acceptable for authentication or may be discarded and a subsequent image captured. Process 1400 may include step 1440 where a user may activate control button 1320 "AUTHENTICATE" such as shown in FIG. 13 and may prompt transfer of the image to a remote server and determination of authentication. Process 1400 may include step 1450, wherein current authentication data derived from the transferred image may be compared to retrieved expected authentication data to determine a match value or probability of being authentic. Based upon the value, process 1400 may report an authentication PASS indication in step 1460, an authentication FAIL indication in step 1470 or an authentication SUSPECT indication in step 1480. The indication may be for example, a colored indication with red for fail and green for pass. Process 1400 may end with step 1490 following indication of authenticity. The authentication system may automatically determine identification of the object to be matched using techniques such as image comparison, accessing online images, or the user may supply identifying information such as object name, type, model, and the like, for example, during step 1410.

The changes described above, and others, may be made in the authentication systems described herein without departing from the scope hereof. For example, although certain examples are described in association with laser marked semiconductor chip packages, it may be understood that the authentication systems described herein may be adapted to other types of objects and other types are marking methodologies. Furthermore, authentication systems as described herein may include one or more types of measurement, characterization, analysis methods or systems. For example, systems and methods discussed herein for laser marked semiconductor chip package authentication may include die, wafer and package level authentication using infrared or Terahertz spectral bands of radiation to penetrate semiconductor chip packages in addition to visible light imaging for authentication of the semiconductor chip packages themselves. Different degrees of resolving power may be appropriate or achievable for each type of authentication performed.

For the semiconductor example, raw wafer vendor and foundry chip manufacturer, wafer segmentation and chip packaging, semiconductor contract manufacturers (CMs) who assemble devices onto circuit boards may be included within the authentication trail and use the defined authentication systems with low cost method of authentication that enables validation of both current production and legacy parts, absent direct participation by the semiconductor manufacturers themselves. Furthermore, the system and methods herein may provide the capability of non-contact validation of parts even after they installation on a circuit board, thereby enabling provenance identification, for example, for systems integrators.

Authentication and identification capability may be provided as a service by maintaining a database of known genuine objects, and charging a low cost subscription fee to contract manufacturers and upstream integrators to access it. In the field, end users may capture images of suspect parts using conventional USB-enabled microscopes, already installed in their facilities, and cloud-based software may be automatically perform identification calculations and feed back to the user confirmation of point of origin.

Figure 15:
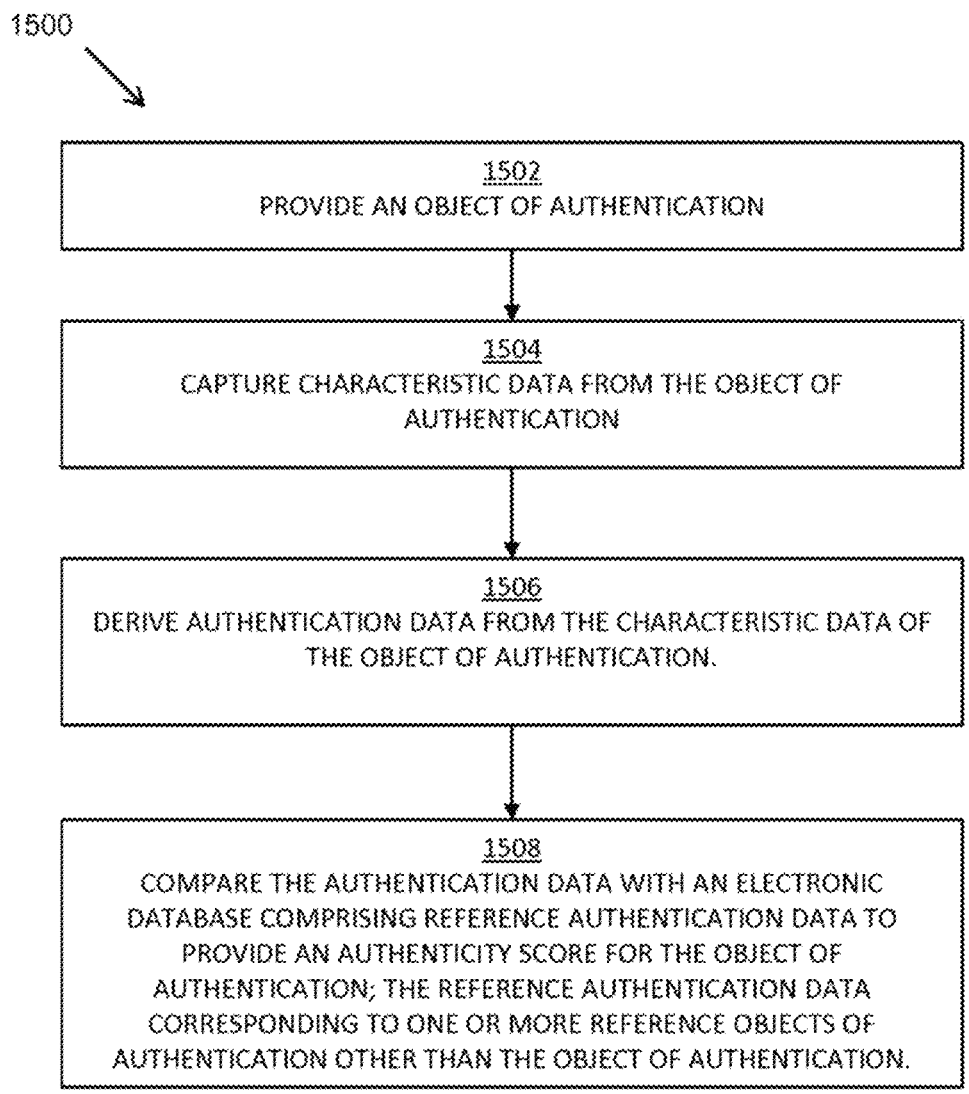
FIG. 15 is a flow diagram of an example method 1500 for authentication.

FIG. 15 is a flow chart of an example method 1500 for determining authenticity. The method may include 1502 providing an object of authentication. The object of authentication may be any tangible thing for which authentication is desired. The method may include 1504 capturing characteristic data from the object of authentication. The method may include 1506 deriving authentication data from the characteristic data of the object of authentication. The method may include 1508 comparing the authentication data with an electronic database including reference authentication data to provide an authenticity score for the object of authentication. The reference authentication data may correspond to one or more reference objects of authentication other than the object of authentication.

Capturing characteristic data from the object of authentication may include capturing two or more sets of characteristic data, e.g., images, and processing or selecting among the sets of characteristic data to determine an improved or desired set of characteristic data. For example, the two or more sets of characteristic data may be averaged or aggregated. A selection may be made among the two or more sets of characteristic data based on noise level, best fit to the reference characteristic data, number of parameters such as in deriving the authentication data as a set of Bezier parameters from the two or more sets of characteristic data, the relative OCR quality or efficiency operative on the two or more sets of characteristic data, and the like. The two or more sets of characteristic data may be captured from different wavelengths, using different characterization methods, and the like.

In some embodiments, the object of authentication and the one or more reference objects of authentication may include articles of manufacture. For example, the characteristic data may be captured from a mark on the article of manufacture. The article of manufacture may be, for example, a marked object such as a laser-marked computer chip. The mark may include a font character or glyph. The articles of manufacture may be laser-marked articles.

In several embodiments, the authentication may include subjecting the object of authentication to one or more of: imaging, profilometry, polarimetry, scatterometry, and microscopy. Deriving the authentication data from the characteristic data may include, for example, analyzing the characteristic data using one or more of: an image transform, statistical analysis, principle component analysis, optical character recognition analysis, font reconstruction, image analysis, polynomial spline fitting, Bezier curve spline fitting, Bezier curve extraction/characterization, Scalable Vector Graphic analysis, Unified Font Object analysis, image registration, wavelet analysis, spatial frequency analysis (e.g. Fourier analysis), and the like. The authentication data may include one or more authentication parameters provided by analyzing the characteristic data. The one or more authentication parameters may define one or more authentication functions, e.g., a Bezier curve or polynomial components thereof.

In various embodiments, comparing the authentication data to the electronic database may include comparing the one or more authentication parameters with one or more reference authentication parameters included by the reference authentication data in the electronic database. Comparing the authentication data to the electronic database may include mathematically determining between the authentication data and the reference authentication data one or more of: a similarity and a difference. Comparing the authentication data to the electronic database may include performing a statistical testing of one or more of the authentication data and the reference authentication data. Comparing the authentication data to the electronic database may include mathematically determining between the authentication data and the reference authentication data one or more of: a similarity and a difference.

In some embodiments, the electronic database may exclude authentication data derived from the object of authentication. The one or more reference objects of authentication may include a plurality of reference objects of authentication belonging to the same family.

In several embodiments, the method may include capturing reference characteristic data from the one or more reference objects of authentication. The method may include deriving the reference authentication data from the reference characteristic data of the one or more reference objects of authentication. The method may include storing the reference authentication data in the electronic database. Deriving the reference authentication data from the reference characteristic data may include analyzing the reference characteristic data using one or more of: an image transform, statistical analysis, principle component analysis, optical character recognition analysis, font reconstruction, image analysis, polynomial spline fitting, Bezier curve spline fitting, Bezier curve extraction/characterization, Scalable Vector Graphic analysis, Unified Font Object analysis, image registration, wavelet analysis, spatial frequency analysis (e.g., Fourier analysis), and the like. The reference authentication data may include one or more reference authentication parameters provided by analyzing the reference characteristic data. The one or more reference authentication parameters may define one or more reference authentication functions. The electronic database may include one or more secondary identifiers may correspond to the one or more reference objects of authentication. The method may include correlating the one or more secondary identifiers with the object of authentication according to the authenticity score. The one or more secondary identifiers may include one or more of: a name, a logo, a trademark, a vendor, a lot number, a date of manufacture, and a marking system description.

In various embodiments, the method may include reporting the authentication score. The authentication score may include one or more of: a Boolean value, a binned value, and a probability. The electronic database may include provenance data associated with the reference authentication data. Comparing the authentication data with the electronic database may include determining a corresponding provenance score of the object of authentication. The provenance data may include manufacturing origin data.

In some embodiments, capturing the characteristic data may include capturing an optical image of the object of authentication. Deriving the authentication data may include performing optical characterization recognition and font reconstruction of the optical image to provide a reconstructed font. Deriving the authentication data may include extracting from the reconstructed font one or more parameters of a polynomial spline or a Bezier curve spline representative of the reconstructed font to provide the authentication data comprising a spline font database. The reference authentication data may be derived from reference characteristic data captured from the one or more reference objects of authentication other than the object of authentication.

In several embodiments, capturing the characteristic data may include capturing an optical image of the object of authentication. Deriving the authentication data may include performing optical characterization recognition and font reconstruction of the optical image to provide a reconstructed font. Deriving the authentication data may include extracting from the reconstructed font one or more parameters of a polynomial spline or a Bezier curve spline representative of the reconstructed font to provide the authentication data comprising a spline font database. The authentication data may include the font Bezier curve parameters corresponding to marking system data. The reference authentication data may include reference marking system data. Comparing the authentication data with the electronic database may include comparing the marking system data with the reference marking system data to provide the authenticity score for the object of authentication. The authenticity score may correspond to a provenance score for the object of authentication. The reference marking system data may include a marking system used to mark the one or more reference objects of authentication.

In various embodiments, capturing the characteristic data may include capturing an optical image of the object of authentication. Deriving the authentication data may include performing optical characterization recognition and font reconstruction of the optical image to provide a reconstructed font. Deriving the authentication data may include extracting from the reconstructed font one or more parameters of a polynomial spline or a Bezier curve spline representative of the reconstructed font to provide the authentication data comprising a spline font database. The authentication data may include the font Bezier curve parameters corresponding to marking system data. The reference authentication data may include reference marking system data. Comparing the authentication data with the electronic database may include comparing the marking system data with the reference marking system data to provide the authenticity score for the object of authentication. The authenticity score may correspond to a provenance score for the object of authentication. The reference marking system data may correspond to a marking system used to mark the one or more reference objects of authentication. The reference marking system data may be derived from statistical testing of the reference authentication data.

In some embodiments, capturing the characteristic data may include capturing an optical image of markings on the object of authentication. Deriving the authentication data may include providing the optical image of the markings for the comparing. The reference authentication data may include at least one reference authentication image corresponding to the one or more reference objects of authentication. Comparing the authentication data with the electronic database may include determining a mathematical similarity or difference between the optical image of the markings and the at least one reference authentication image to provide the authenticity score for the object of authentication. The authenticity score may indicate whether the object of authentication has a same origin of manufacture, e.g., provenance, as the one or more reference objects of authentication.

In several embodiments, the object of authentication may include a solid form. As used herein, a solid form is a shape defined by a boundary. For example, solid forms may include font characters, glyphs, tool marking such as laser markings, and the like. Capturing the characteristic data from the object of authentication may include capturing the characteristic data from a boundary of the solid form. The characteristic data may correspond to one or more of: an authenticity of the solid form and a provenance of the solid form. Deriving authentication data from the characteristic data of the object of authentication may include analyzing the characteristic data to determine a plurality of arc segments. Each arc segment in the plurality of arc segments may correspond to at least one member of the characteristic data. The authentication data may include the plurality of arc segments. Comparing the authentication data with the electronic database including the reference authentication data to provide the authenticity score for the object of authentication may include comparing the plurality of arc segments to a plurality of reference arc segments include by the reference authentication data in the electronic database.

In some embodiments, analyzing the characteristic data to determine a plurality of arc segments may explicitly exclude using a neural network. In some embodiments, capturing characteristic data of a boundary of the solid form may explicitly exclude using a neural network. Further, for example, the method may explicitly exclude using a neural network.

In several embodiments, providing the solid form to be analyzed may include providing a marked object including the solid form. The solid form may include a font character or glyph. Identifying the characteristic data may include obtaining an image of the solid form on the marked object. The characteristic data may correspond to characteristic data as described herein. The characteristic data, e.g., an optical image of the characteristic data, may be examined using one or more of: image transforms, statistical analyses, principle component analyses, optical character recognition analyses and font reconstruction, image analyses, polynomial spline fitting, Bezier curve extraction, characterization by means of Bezier curves, Scalable Vector Graphics or Unified Font Objects, image registration, wavelet analyses and spatial frequency analysis. For example, the arc segments may be suitable for examination using any of the preceding techniques, e.g., Bezier curve extraction.

In some embodiments, the characteristic data may be analyzed using one or more of the preceding techniques to provide authentication data as described herein. For example, the plurality of arc segments may correspond to authentication data as described herein. Likewise, a plurality of reference arc segments may correspond to reference authentication data as described herein.

In various embodiments, the method may include capturing the characteristic data from one or more of an exterior boundary of the solid form and an interior boundary of the solid form. The characteristic data may collectively describe a closed contour circumscribing the boundary of the solid form. In some embodiments, the characteristic data may collectively describe an open contour delineating a portion of the boundary of the solid form.

In some embodiments, the solid form may be included by a marked object, e.g., the marked object described herein. For example, the solid form may be a glyph or font character marked on the object. Providing the solid form may include providing the marked object including the solid form. Providing the solid form may include marking an unmarked object to form the marked object, e.g., using a marking system as described herein.

In several embodiments, providing the solid form may include identifying at least one secondary identifier associated with the solid form. The at least one secondary identifier may include one or more of: name, vendor, lot number, date of manufacture, marking system description, and the like. For example, the name may be the name of the marked object. The vendor may be the manufacturer or seller of the marked object. The date of manufacture may correspond to the marked object. The marking system description may describe a marking system used to mark the object with the solid form, e.g., a laser marking system. The at least one secondary identifier associated with the solid form may include exogenous data associated with the solid form. The at least one secondary identifier associated with the solid form may include data incorporated in the solid form. For example, the solid form may include or be part of a plurality of glyphs, e.g., font characters, that recite or correspond to the name, the vendor, the lot number, the date of manufacture, and the like.

In various embodiments, identifying the characteristic data may include measuring the solid form using one or more of: imaging, profilometry, scatterometry, polarimetry, microscopy, and the like.

In some embodiments, determining the plurality of arc segments may include calculating a plurality of splines corresponding to the plurality of arc segments. Each spline may be calculated as a spline representation corresponding to the plurality of arc segments. The spline may be characterized by a plurality of polynomial functions. Further, calculating each spline in the plurality of splines may include dividing each corresponding arc segment into a plurality of arc sub-segments. Each plurality of arc sub-segments may be defined by a corresponding plurality of knots along each arc segment. Calculating each spline in the plurality of splines may include determining a plurality of knot coordinates in 2D space corresponding to the plurality of knots. The plurality of knot coordinates may be sufficient to specify a plurality of parameters of each corresponding spline. Each plurality of knots may be, for example, equidistant on an interval spanned by a corresponding parametric variable. The corresponding parametric variable may be effective to generate the plurality of knots along each corresponding arc segment.

In several embodiments, calculating each spline in the plurality of splines may include calculating a plurality of polynomial functions over a parametric variable of a fixed domain corresponding to each arc segment. The method may include calculating the plurality of polynomial functions in the form of a Bezier curve corresponding to each arc segment. The Bezier curve may be, for example, cubic or quadratic.

In some embodiments, the method may include comparing the solid form to at least one reference solid form by a feature to feature comparison of the characteristic data of the solid form to reference characteristic data of the at least one reference solid form. For example, the method may include providing the at least one reference solid form. The method may include analyzing the at least one reference solid form to identify the reference characteristic data of the reference boundary of the at least one reference solid form. The method may include determining a plurality of reference arc segments. Each reference arc segment in the plurality of reference arc segments may correspond to at least one member of the reference characteristic data.

In various embodiments, comparing the characteristic data to the reference characteristic data may include projecting the characteristic data according to location on the boundary of the solid form onto the reference boundary of the reference solid form. The method may include projecting the reference characteristic data according to location on the reference boundary of the reference solid form onto the boundary of the solid form. The method may include projecting the characteristic data according to location on the boundary of the solid form onto the reference boundary of the reference solid form. The method may include locating each of the characteristic data at a corresponding intersection. Each corresponding intersection may be between a line perpendicular to the boundary of the solid form and a nearest neighbor location on the reference boundary of the reference solid form. The method may include projecting the reference characteristic data according to location on the reference boundary of the reference solid form onto the boundary of the solid form. The method may include locating each of the reference characteristic data at a corresponding reference intersection. Each corresponding reference intersection may be between a line perpendicular to the reference boundary of the reference solid form and a nearest neighbor location on the boundary of the solid form.

In some embodiments, comparing the characteristic data to the reference characteristic data may include projecting the characteristic data according to location on the boundary of the solid form onto the reference boundary of the reference solid form. The method may include locating each of the characteristic data by mapping a nearest neighbor point on the reference boundary of the reference solid form with a corresponding point of the characteristic data. The method may include projecting the reference characteristic data according to location on the reference boundary of the reference solid form onto the boundary of the solid form. The method may include locating each of the reference characteristic data by mapping a nearest neighbor point on the boundary of the solid form with a corresponding point of the reference characteristic data.

In several embodiments, comparing the solid form to the at least one reference solid form by the feature to feature comparison may include one or more of (A) and (B). Method portion (A) may include providing a plurality of reference arc segments. Each reference arc segment in the plurality of reference arc segments may correspond to at least one member of the reference characteristic data. Each reference arc segment in the plurality of reference arc segments may include a beginning reference point, an ending reference point, and at least one intermediate reference knot. Method portion (A) may include determining proximity of a reference point on the reference solid form to the beginning and ending reference points of each reference arc segment by projecting the beginning and ending reference points and the at least one intermediate reference knot of each reference arc segment onto the boundary of the solid form. Method portion (A) may include determining proximity of a reference point on the reference solid form to the beginning and ending reference points of each reference arc segment by locating each of the plurality of reference arc segments to determine the proximity. Locating each of the plurality of reference arc segments to determine the proximity may proceed according to a corresponding intersection between a line perpendicular to the boundary of the solid form and a nearest neighbor location on the reference boundary of the reference solid form. Locating each of the plurality of reference arc segments to determine the proximity may proceed according to a nearest neighbor point mapped on the reference boundary with a corresponding point of the characteristic data on the boundary. In method portion (B), each arc segment in the plurality of arc segments may include a beginning point, an ending point, and at least one intermediate knot. Method portion (B) may include determining proximity of a point on the solid form to the beginning and ending points of each arc segment by projecting the beginning and ending points and the at least one intermediate knot of each arc segment onto the reference boundary of the reference solid form. Method portion (B) may include determining proximity of a point on the solid form to the beginning and ending points of each arc segment by locating each of the plurality of arc segments to determine the proximity. Locating the plurality of arc segments to determine the proximity may proceed according to a corresponding intersection between a line perpendicular to the reference boundary of the reference solid form and a nearest neighbor location on the boundary of the solid form. Locating the plurality of arc segments to determine the proximity may proceed according to a nearest neighbor point mapped on the boundary with a corresponding point of the plurality of reference arc segments on the reference boundary.

For example, for each arc segment, the corresponding beginning point, ending point, and knot may correspond to authentication parameters as described herein. Similarly, for each reference arc segment, the corresponding beginning reference point, ending reference point, and reference knot may correspond to reference authentication parameters as described herein. Comparing the solid form and the reference solid form may include comparing such authentication parameters to such reference authentication parameters, e.g., by determining a mathematical similarity or difference between the authentication data and the reference authentication data. For example, comparing the solid form and the reference solid form may include comparing the beginning point, ending point, and knot corresponding to each arc segment to the beginning reference point, ending reference point, and reference knot corresponding to each reference arc segment.

In various embodiments, distinguishing the solid form from the at least one reference solid form may include calculating an area between the at least one arc segment and the at least one reference arc segment. The beginning point and the ending point of each arc segment may respectively be nearest neighbors to the reference beginning point and the reference ending point of each corresponding reference arc segment. The reference beginning point and the reference ending point of each corresponding reference arc segment respectively may be characterized by a normal beginning reference line and a normal ending reference line. The method may include determining the beginning point and the ending point of each corresponding arc segment from respective intersections of each arc segment with the normal beginning reference line and the normal ending reference line. For example, the method may include calculating areas broken down by the beginning point of the reference arc to a first control-point knot, from the first control point knot to a second control point knot (e.g., in a cubic Bezier spline), and from the second control point knot to the ending point, and the like. For example, a quadratic Bezier curve may include two features per arc segment, a cubic Bezier curve may include three features per arc segment, and the like.

In some embodiments, the number of arc segments for the plurality of arc segments may be equal to a number of reference arc segments of the plurality of reference arc segments.

In several embodiments, the method may include determining the beginning point and the ending point of each corresponding arc segment from respective intersections of each arc segment with the normal beginning reference line and the normal ending reference line. The characteristic data may belong to one or more of: an unknown authenticity and an unknown provenance. The reference characteristic data may belong to a corresponding one or more of: a known authenticity and a known provenance.

In various embodiments, comparing the solid form to the at least one reference solid form may include classifying the solid form as belonging to or excluded from one or more of: the known authenticity and the known provenance. Accordingly, classifying the solid form may determine authenticity or provenance of the solid form, e.g., corresponding to a marked object including the solid form. Classifying the solid form as belonging to or excluded from one or more of the known authenticity and the known provenance may correspond to determining a class value indicative of belonging or exclusion. For example, classifying the solid form as belonging to or excluded from one or more of the known authenticity and the known provenance may include determining an authentication value as described herein, a provenance value as described herein, and the like. Classifying the solid form as belonging to or excluded from one or more of the known authenticity and the known provenance may correspond to reporting the class value indicative of belonging or exclusion. The class value may include, for example, a Boolean value or a probability indicative of belonging or exclusion. For example, the class value may include: a Boolean value "true" value indicating authenticity or provenance of a corresponding solid form; a Boolean value "false" value contradicting authenticity or provenance of a corresponding solid form; a probability of authenticity or provenance of a corresponding solid form; and the like.

In some embodiments, the method may include providing an electronic database including the reference authentication data. The electronic database including the reference authentication data may include a representation of the reference solid form according to one or more of: the known authenticity and the known provenance. The method may include comparing the solid form to the at least one reference solid form by, for example, classifying the solid form with respect to the electronic database. The solid form may be classified as belonging to or excluded from one or more of: the known authenticity and the known provenance. For example, the electronic database may be stored in and accessed from the data storage described herein. The electronic database may include or correspond to the reference authentication data described herein. The electronic database may include reference authentication parameters as described herein, e.g., the plurality of reference arc segments and corresponding beginning reference points, ending reference points, and reference knots. The representation of the reference solid form may correspond to the plurality of reference solid forms and the plurality of reference solid forms may be related by class, e.g., derived from a plurality of marked objects from the same family as described herein.

In several embodiments, the method may include providing an electronic database including the reference authentication data. The electronic database may include a representation of a synthetic reference form according to one or more of: the known authenticity and the known provenance. The synthetic reference form may be derived from a plurality of the reference solid forms. The method may include comparing the solid form to the at least one reference solid form by classifying the solid form with respect to the electronic database. The solid form may be classified as belonging to or excluded from one or more of: the known authenticity and the known provenance. Classifying the solid form may include using one or more of: a clustering formulation and a classifier. Classifying the solid form may include one or more of: K-means clustering, Neyman-Pearson classifying, Kolmogorov-Smirnoff classifying, and Mann-Whitney classifying.

In several embodiments, the method may include providing a plurality of reference solid forms collectively belonging to a known authenticity and/or a known provenance. The method may include identifying a plurality of reference characteristic features corresponding to a plurality of reference boundaries of the plurality of reference solid forms. The method may include combining the reference characteristic data of the plurality of reference solid forms to create a synthetic reference solid form associated with a plurality of synthetic reference characteristic features. The synthetic reference solid form may be representative of one or more of: the known authenticity and the known provenance. The method may include comparing the solid form to the synthetic reference solid form by comparing the characteristic data of the solid form to the plurality of synthetic reference characteristic features of the synthetic reference solid form. The method may include calculating a statistical distribution of the reference characteristic data may correspond to the plurality of reference solid forms. The statistical distribution may be calculated by comparing individual members of the plurality of reference solid forms with the synthetic reference solid form. The statistical distribution of the reference characteristic data may include a standard deviation of corresponding reference characteristic features. The standard deviation of corresponding reference characteristic features may be among the plurality of reference solid forms with respect to a corresponding member of the plurality of synthetic reference characteristic features of the synthetic reference solid form. The statistical distribution of the reference characteristic data may include higher order moments of corresponding reference characteristic features. The corresponding reference characteristic features may be among the plurality of reference solid forms with respect to a corresponding member of the plurality of synthetic reference characteristic features of the synthetic reference solid form.

In various embodiments, the method may include providing a plurality of the solid forms to be analyzed. The plurality of solid forms may collectively belong to an unknown authenticity and/or an unknown provenance. The method may include identifying a plurality of the characteristic features corresponding to a plurality of the reference boundaries of the plurality of solid forms. The method may include combining the characteristic data of the plurality of solid forms to create a synthetic solid form associated with a plurality of synthetic characteristic features. The synthetic solid form may be representative of one or more of: the unknown authenticity and the unknown provenance. The method may include calculating a statistical distribution of the characteristic data corresponding to the plurality of solid forms by comparing individual members of the plurality of solid forms with the synthetic solid form. The statistical distribution of the characteristic data may include a standard deviation of corresponding characteristic features. The standard deviation of corresponding characteristic features may be among the plurality of solid forms with respect to a corresponding member of the plurality of synthetic characteristic features of the synthetic solid form. The statistical distribution of the characteristic data may include higher order moments of corresponding characteristic features. The higher order moments of corresponding characteristic features may be among the plurality of solid forms with respect to a corresponding member of the plurality of synthetic characteristic features of the synthetic solid form.

Figure 16:
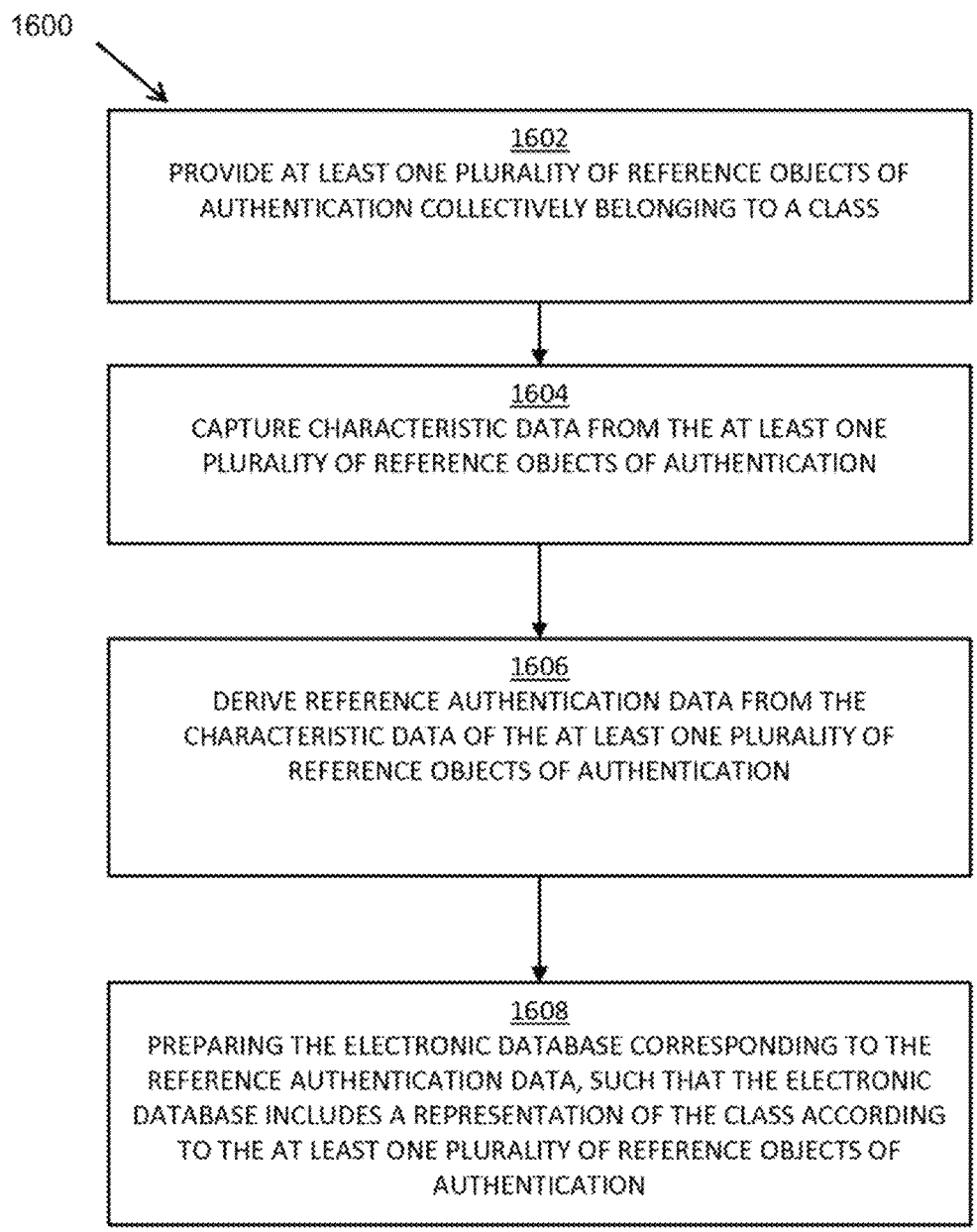
FIG. 16 is a flow diagram of an example method 1600 for creating an electronic database including reference authentication data.

FIG. 16 is a flow chart of an example method 1600 for creating an electronic database. The method may include 1602 providing at least one plurality of reference objects of authentication collectively belonging to a class. The method may include 1604 capturing characteristic data from the at least one plurality of reference objects of authentication. The method may include 1606 deriving reference authentication data from the characteristic data of the at least one plurality of reference objects of authentication. The method may include 1608 preparing the electronic database may correspond to the reference authentication data. The electronic database may include a representation of the class according to the at least one plurality of reference objects of authentication.

In some embodiments, the class may include one or more of: a known authenticity class, an unknown authenticity class, a known provenance class, and an unknown provenance class. The electronic database may include a representation of one or more of: the known authenticity class, the unknown authenticity class, the known provenance class, and the unknown provenance class. The class may include one or more of: an unknown authenticity class and an unknown provenance class. The method may include classifying the at least one plurality of reference objects of authentication with respect to exogenous known class data such that the electronic database includes a representation of the class as one or more of: a known authenticity class and a known provenance class. The exogenous class data may include secondary identifiers, as described herein, or other information about a class derived from a source other than the characteristic data.

In several embodiments, the method may include conducting the providing, the identifying, the determining, and the preparing with respect to two or more pluralities of reference objects of authentication. Each plurality of the two or more pluralities of reference objects of authentication may collectively belong to a different class, such that the electronic database may include representations of each different class according to the two or more pluralities of reference objects of authentication.

In various embodiments, the method may include determining at least one synthetic reference object of authentication corresponding to the at least one plurality of reference objects of authentication such that the at least one synthetic reference object of authentication may be representative of the class. Determining the at least one synthetic reference object of authentication may include combining the reference authentication data to form corresponding synthetic reference authentication data. Determining the at least one synthetic reference object of authentication may include combining the reference characteristic data to form corresponding synthetic reference characteristic data. Preparing the electronic database may include collecting the synthetic reference data, such that the electronic database may include a representation of the class according to the at least one synthetic reference object of authentication.

In some embodiments, the method may include respectively calculating a statistical distribution of the characteristic data corresponding to the at least one plurality of reference objects of authentication. Calculating a statistical distribution may include comparing individual members of the at least one plurality of reference objects of authentication with the at least one synthetic reference object of authentication. Preparing the electronic database may include incorporating the statistical distribution such that the electronic database may include a representation of the class characterized by the statistical distribution with respect to the at least one synthetic reference object of authentication. Each statistical distribution may include a standard deviation. Each statistical distribution may include a plurality of higher order moments.

Figure 17:
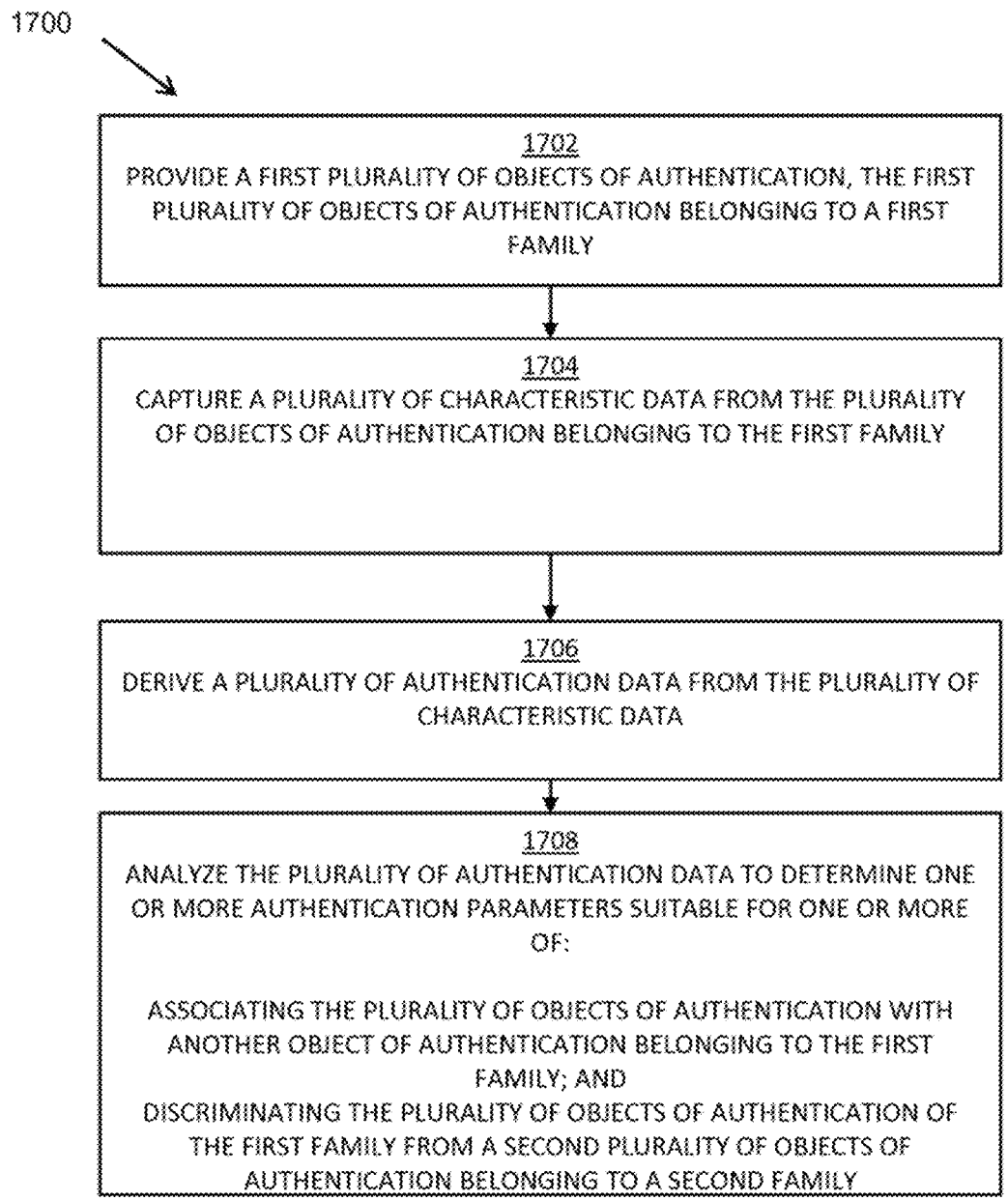
FIG. 17 is a flow diagram of an example method 1700 for defining authentication data.

FIG. 17 is a flow diagram of an example method 1700 for defining authentication data. The method may include 1702 providing a first plurality of objects of authentication. The first plurality of objects of authentication may belong to a first family. The method may include 1704 capturing a plurality of characteristic data from the plurality of objects of authentication belonging to the first family. The method may include 1706 deriving a plurality of authentication data from the plurality of characteristic data. The method may include 1708 analyzing the plurality of authentication data to determine one or more authentication parameters. The one or more authentication parameters may be suitable for associating the plurality of objects of authentication with another object of authentication belonging to the first family. The one or more authentication parameters may be suitable for discriminating the plurality of objects of authentication of the first family from a second plurality of objects of authentication belonging to a second family.

In various embodiments, providing the plurality of objects of authentication may include providing an unmarked object of authentication and marking the unmarked object of authentication. The method may include providing the second plurality of objects of authentication. The second plurality of objects of authentication may belong to the second family. Capturing the plurality of characteristic data may include capturing the plurality of characteristic data from the second plurality of objects of authentication belonging to the second family. Analyzing may include performing statistical testing to determine the authentication parameters. Analyzing may include performing statistical testing to determine the separation of the first and second families in a vector space of the authentication parameters. Analyzing may include performing an optimization to choose vectors suitable for maximizing the distance between the first and second families. The vectors may be suitable for discriminating the plurality of objects of authentication of the first family from the second plurality of objects of authentication belonging to the second family.

Figure 18:
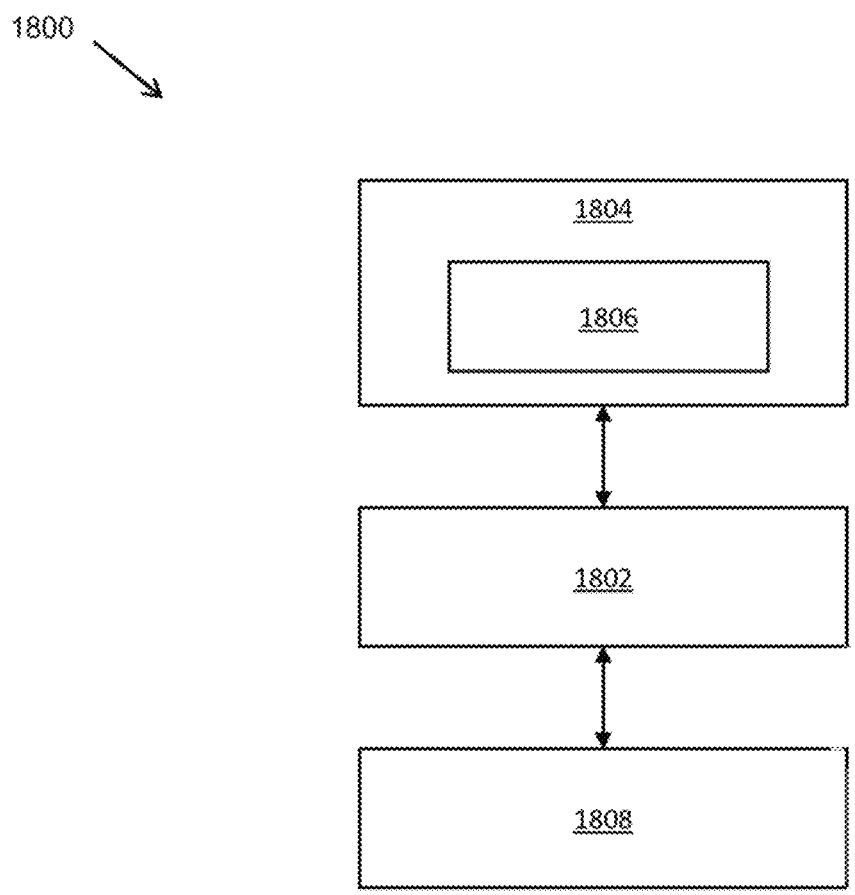
FIG. 18 is a block diagram of an example system 1800 for authentication.

FIG. 18 is a block diagram of a system 1800 for determining authenticity. System 1800 may include a characterization module 1802 configured for capturing characteristic data from an object of authentication. System 1800 may include a data storage module 1804 configured to store an electronic database 1806 including reference authentication data. System 1800 may include a processor 1808 operatively coupled to characterization module 1802 and data storage module 1804. Processor 1808 may be programmed to operate characterization module 1802 to capture the characteristic data from the object of authentication. Processor 1808 may be programmed to derive authentication data from the characteristic data of the object of authentication. Processor 1808 may be programmed to compare the authentication data with the electronic database 1806 including the reference authentication data to provide an authenticity score for the object of authentication. Processor 1808 may be programmed to access the data storage module 1804 to store and retrieve one or more of: the authentication data, the electronic database 1806 including the reference authentication data, the characteristic data from the object of authentication, and the authenticity score.

In various embodiments, characterization module 1802 may include one or more of: an imager, a profilometer, a scatterometer, a polarimeter, and a microscope. Processor 1808 may include one or more of: a local processor, an embedded processor, a distributed processor, a smart phone, a smart watch, a personal computer; and a tablet computer. Processor 1808 may include a portable computing device including one or more of: a smart phone, a smart watch, a personal computer, and a tablet computer. Data storage module 1804 may include one or more of: a memory included by the portable computing device and a remote storage system (e.g., network storage, cloud storage, and the like) accessed by the portable computing device. Characterization module 1802 may include an optical imager included by the portable computing device, e.g., a smart phone camera.

In some embodiments, the reference authentication data may correspond to one or more reference objects of authentication other than the object of authentication. The object of authentication and the one or more reference objects of authentication may include articles of manufacture. The object of authentication may include an article of manufacture and processor 1808 may be programmed to operate characterization module 1802 to capture the characteristic data from a mark on the article of manufacture. The mark may include a font character, glyph, laser marking, and the like. For example, the articles of manufacture may be laser-marked articles.

In several embodiments, processor 1808 may be programmed to derive the authentication data from the characteristic data including analyzing the characteristic data. The analyzing may include using one or more of: an image transform, statistical analysis, principle component analysis, optical character recognition analysis, font reconstruction, image analysis, polynomial spline fitting, Bezier curve spline fitting, Bezier curve extraction/characterization, Scalable Vector Graphic analysis, Unified Font Object analysis, image registration, wavelet analysis, spatial frequency analysis (e.g., Fourier analysis), and the like. Processor 1808 may be programmed to derive the authentication data including one or more authentication parameters by analyzing the characteristic data. Processor 1808 may be programmed to provide the one or more authentication parameters defining one or more authentication functions. Processor 1808 may be programmed to compare the authentication data to the electronic database 1806 by comparing the one or more authentication parameters with one or more reference authentication parameters. The one or more reference authentication parameters may be included by the reference authentication data in the electronic database 1806. Processor 1808 may be programmed to compare the authentication data to the electronic database 1806 by mathematically determining between the authentication data and the reference authentication data one or more of: a similarity and a difference. Processor 1808 may be programmed to compare the authentication data to the electronic database 1806 by performing a statistical testing of one or more of the authentication data and the reference authentication data. Processor 1808 may be programmed to compare the authentication data to the electronic database 1806 by mathematically determining between the authentication data and the reference authentication data one or more of: a similarity and a difference. Processor 1808 may be programmed to access the electronic database 1806 excluding authentication data derived from the object of authentication. The one or more reference objects of authentication may include a plurality of reference objects of authentication belonging to the same family.

In various embodiments, processor 1808 may be programmed to capture reference characteristic data from the one or more reference objects of authentication. Processor 1808 may be programmed to derive the reference authentication data from the reference characteristic data of the one or more reference objects of authentication. Processor 1808 may be programmed to store the reference authentication data in the electronic database 1806 in the data storage module 1804. Processor 1808 may be programmed to derive the reference authentication data from the reference characteristic data including analyzing the reference characteristic data using one or more of: an image transform, statistical analysis, principle component analysis, optical character recognition analysis, font reconstruction, image analysis, polynomial spline fitting, Bezier curve spline fitting, Bezier curve extraction/characterization, Scalable Vector Graphic analysis, Unified Font Object analysis, image registration, wavelet analysis, spatial frequency analysis (e.g., Fourier analysis), and the like. Processor 1808 may be programmed to provide the reference authentication data including one or more reference authentication parameters by analyzing the reference characteristic data. Processor 1808 may be programmed to provide the one or more reference authentication parameters defining one or more reference authentication functions. Processor 1808 may be programmed to access the electronic database 1806 including one or more secondary identifiers corresponding to the one or more reference objects of authentication. Processor 1808 may be programmed to correlate the one or more secondary identifiers with the object of authentication according to the authenticity score. The one or more secondary identifiers may include one or more of: a name, a logo, a trademark, a vendor, a lot number, a date of manufacture, and a marking system description.

In some embodiments, processor 1808 may be programmed to report the authentication score. The authentication score may include one or more of: a Boolean value, a binned value, and a probability. Processor 1808 may be programmed to access the electronic database 1806 including provenance data associated with the reference authentication data. Processor 1808 may be programmed to compare the authentication data with the electronic database 1806 to determine a provenance score of the object of authentication. The provenance data may include manufacturing origin data.

In several embodiments, processor 1808 may be programmed to capture the characteristic data by capturing an optical image of the object of authentication. Processor 1808 may be programmed to derive the authentication data by performing optical characterization recognition and font reconstruction of the optical image to provide a reconstructed font. Processor 1808 may be programmed to derive the authentication data by extracting from the reconstructed font one or more parameters of a polynomial spline or a Bezier curve spline representative of the reconstructed font to provide the authentication data comprising a spline font database. The reference authentication data may be derived from reference characteristic data captured from the one or more reference objects of authentication other than the object of authentication.

In various embodiments, processor 1808 may be programmed to capture the characteristic data by capturing an optical image of the object of authentication. Processor 1808 may be programmed to derive the authentication data by performing optical characterization recognition and font reconstruction of the optical image to provide a reconstructed font. Processor 1808 may be programmed to derive the authentication data by extracting from the reconstructed font one or more parameters of a polynomial spline or a Bezier curve spline representative of the reconstructed font to provide the authentication data comprising a spline font database. The authentication data may include the font Bezier curve parameters corresponding to marking system data. The reference authentication data may include reference marking system data. Processor 1808 may be programmed to compare the authentication data with the electronic database 1806 by comparing the marking system data with the reference marking system data to provide the authenticity score for the object of authentication. The authenticity score may correspond to a provenance score for the object of authentication. The reference marking system data may correspond to a marking system used to mark the one or more reference objects of authentication.

In some embodiments, processor 1808 may be programmed to capture the characteristic data by capturing an optical image of the object of authentication. Processor 1808 may be programmed to derive the authentication data by performing optical characterization recognition and font reconstruction of the optical image to provide a reconstructed font. Processor 1808 may be programmed to derive the authentication data by extracting from the reconstructed font one or more parameters of a polynomial spline or a Bezier curve spline representative of the reconstructed font to provide the authentication data comprising a spline font database. The authentication data may include the font Bezier curve parameters corresponding to marking system data. The reference authentication data may include reference marking system data. Processor 1808 may be programmed to compare the authentication data with the electronic database 1806, by comparing the marking system data with the reference marking system data to provide the authenticity score for the object of authentication. The authenticity score may correspond to a provenance score for the object of authentication. The reference marking system data may correspond to a marking system used to mark the one or more reference objects of authentication. The reference marking system data may be derived from statistical testing of the reference authentication data.

In several embodiments, processor 1808 may be programmed to capture the characteristic data by capturing an optical image of the object of authentication. The reference authentication data may include at least one reference authentication image corresponding to the one or more reference objects of authentication. Processor 1808 may be programmed to derive the authentication data by providing the optical image of the markings for the comparing compare the authentication data with the electronic database 1806 by determining a mathematical similarity or difference between the optical image of the markings and the at least one reference authentication image to provide the authenticity score for the object of authentication. The authenticity score may indicate whether the object of authentication has a same origin of manufacture, e.g., provenance, as the one or more reference objects of authentication.

FIG. 19 is a block diagram of an example tangible computer-readable medium 1900 having instructions 1902 stored thereon for controlling a processor. Instructions 1902 may control the processor to operate the characterization module to capture the characteristic data from the object of authentication. Instructions 1902 may control the processor to derive authentication data from the characteristic data of the object of authentication. Instructions 1902 may control the processor to compare the authentication data with the electronic database including the reference authentication data to provide an authenticity score for the object of authentication. Instructions 1902 may control the processor to access the data storage module to store and retrieve one or more of: the authentication data, the electronic database including the reference authentication data, the characteristic data from the object of authentication, and the authenticity score.

In several embodiments, instructions 1902 may be configured to control the measurement system including one or more of: an imager, a profilometer, a scatterometer, a polarimeter, and a microscope. Instructions 1902 may be configured to control the processor including one or more of: a local processor, an embedded processor, a distributed processor, a smart phone, a smart watch, a personal computer; and a tablet computer.

Instructions 1902 may be configured to control the processor, e.g., as incorporated into aa portable computing device, such as one or more of: a smart phone, a smart watch, a personal computer, and a tablet computer. Instructions 1902 may be configured to control the processor to access the data storage. The data storage may include one or more of: a memory included by the portable computing device and a remote or storage system accessed by the portable computing device. Instructions 1902 may be configured to control the processor to control the measurement system, e.g., an optical imager included by the portable computing device. For example, instructions 1902 may be incorporated into a smart phone as a suitable set of program instructions or "app" for operating a processor, a memory, and a camera of the smart phone. Instructions 1902 may be configured to control the processor to operate a marking system to mark solid forms on objects, e.g., any of the marking systems described herein, such as a laser marking device.

In several embodiments, instructions 1902 may be configured to carry out one or more of any of the methods described herein for authentication, preparing an electronic database including the reference authentication data, and the like.

Example 1: Image Capture and Pre-Treatment

Figure 20:
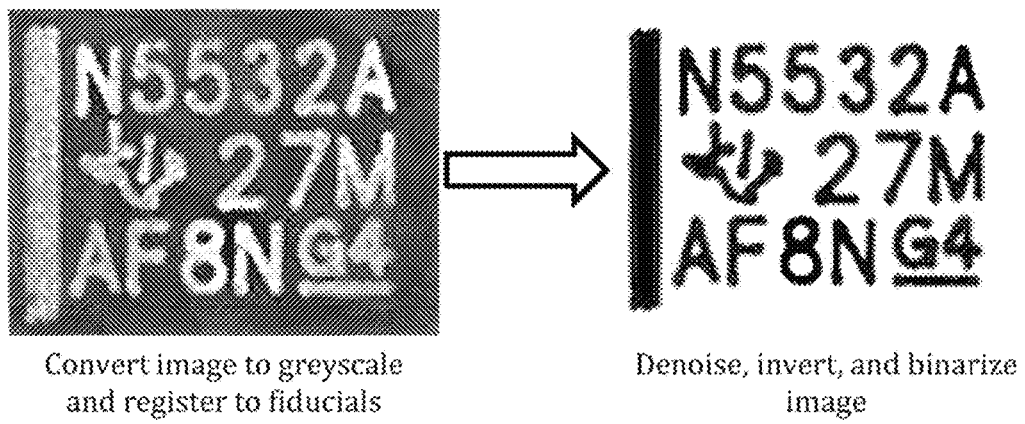
FIG. 20 shows images of individual semiconductor packages and corresponding binarized and rendered black-on-white representations.

Images of individual semiconductor packages were captured using a 1 Mb USB camera connected to a laptop. The images were converted to greyscale and registered to common fiducials, then binarized and rendered as black-on-white representations, as shown in FIG. 20. The representations were analyzed using ClearScan and Font Forge as described above to generate font files including collections of Bezier curves associated with each individual character on each part.

Example 2: Creation of a Template

Figure 21:
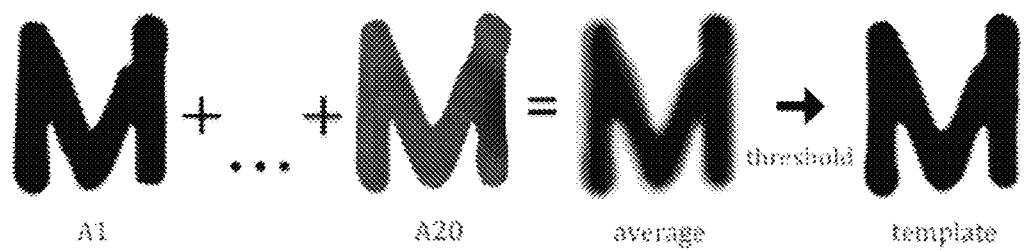
FIG. 21 illustrates averaging and thresholding of images to generate a template glyph.

A collection of images from a common source was averaged and thresholded to generate a template glyph, as shown in FIG. 21. The template glyph itself was described by a collection of Bezier curves. The use of an explicit glyph template as a reference in this example may be contrasted with a neural network analysis approach, where images are fed into a neural network to train on reference material, but where no reference template exists outside of the neural network. In this Example, the template was represented as a series of Bezier curves. Because the template was explicitly defined, the template is suitable for comparison against a challenge part by any of numerous different classifiers.

Example 3: Comparison Against a Classifier

Figure 22:
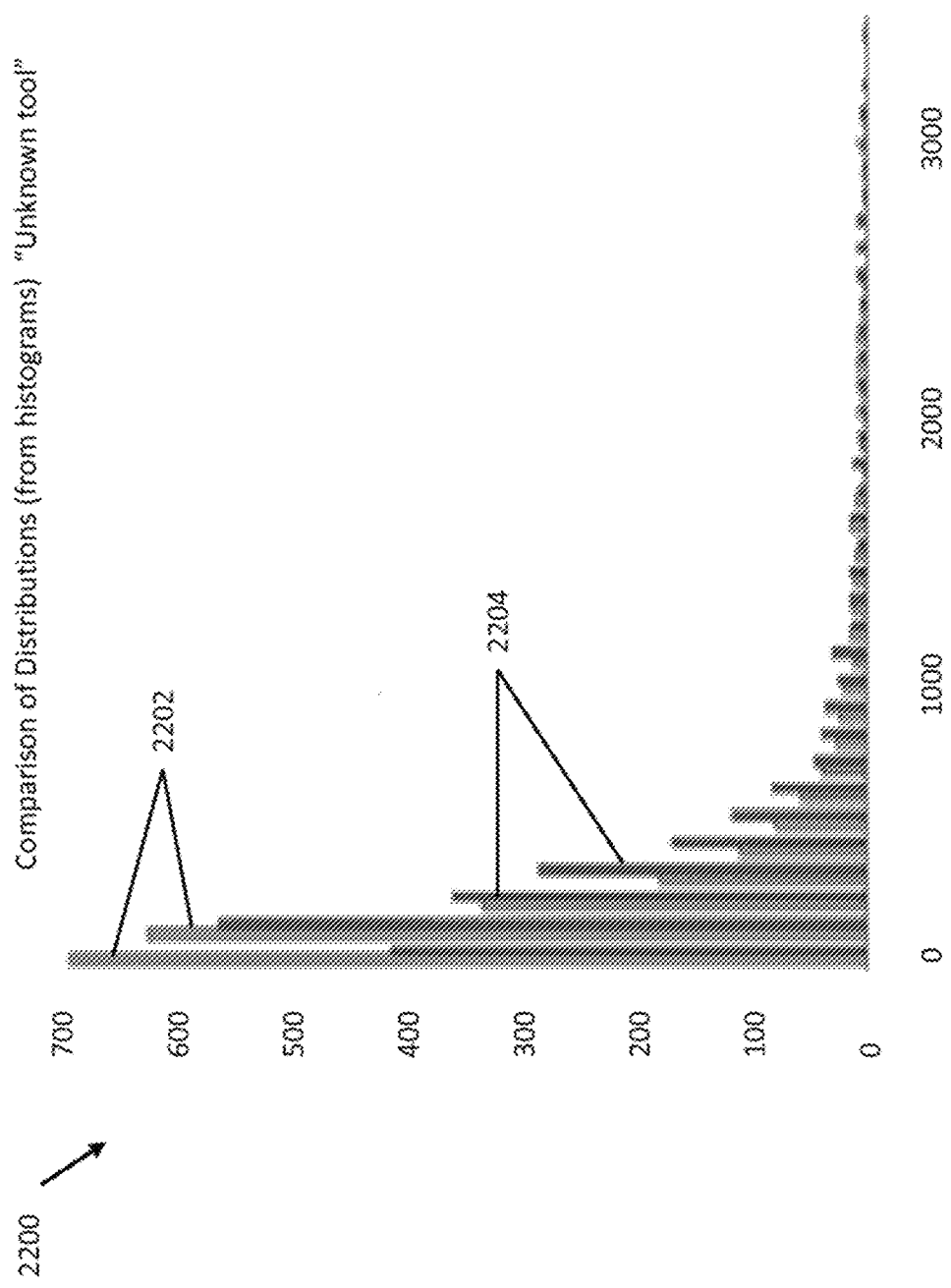
FIG. 22 is a graph of area differences at each control point between a test part and a template, calculated and rank ordered.

The area differences at each control point between the test part and the template were calculated and rank ordered, as shown in graph 2100 in FIG. 22. The statistical relevance of the difference between test and template 2102 versus control and template 2104 was compared using a Mann-Whitney test. The authenticity of the test part was validated by comparison against an acceptable error threshold, for example 95% confidence that the part may be not a false positive. If the comparison exceeds 95% confidence, the part was deemed authentic; if below this threshold, the part was deemed inauthentic. The selection of the exact threshold value may vary from application to application.

It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method for determining authenticity, comprising:
providing an object of authentication;
capturing characteristic data from the object of authentication, comprising capturing an optical image of the object of authentication, comprising subjecting the object of authentication to one or more of: imaging, profilometry, polarimetry, scatterometry, and microscopy;
deriving authentication data from the characteristic data of the object of authentication, comprising:
performing optical characterization recognition and font reconstruction of the optical image to provide a reconstructed font;
extracting from the reconstructed font one or more parameters of a polynomial spline or a Bezier curve spline representative of the reconstructed font to provide the authentication data comprising a spline font database, the authentication data comprising the spline font database corresponding to marking system data; and
comparing the authentication data with an electronic database comprising reference authentication data to provide an authenticity score for the object of authentication,
the reference authentication data corresponding to one or more reference objects of authentication other than the object of authentication, the reference authentication data comprising reference marking system data, the reference marking system data: corresponding to a marking system used to mark the one or more reference objects of authentication; and being derived from statistical testing of the reference authentication data, and
comparing the authentication data with the electronic database comprising comparing the marking system data with the reference marking system data to provide the authenticity score for the object of authentication.

2. The method of claim 1, capturing the characteristic data from the object of authentication further comprising subjecting the object of authentication to spectrometry.

3. The method of claim 1, deriving the authentication data from the characteristic data comprising analyzing the characteristic data using one or more of: an image transform, statistical analysis, principle component analysis, optical character recognition analysis, font reconstruction, image analysis, polynomial spline fitting, Bezier curve spline fitting, Bezier curve extraction/characterization, Scalable Vector Graphic analysis, Unified Font Object analysis, image registration, wavelet analysis, and spatial frequency analysis.

4. The method of claim 1, comparing the authentication data to the electronic database comprising:
performing statistical testing of one or more of the authentication data and the reference authentication data; and
mathematically determining between the authentication data and the reference authentication data one or more of: a similarity and a difference.

5. The method of claim 1, the electronic database excluding authentication data derived from the object of authentication.

6. The method of claim 1, the one or more reference objects of authentication comprising a plurality of reference objects of authentication belonging to the same family.

7. The method of claim 1, further comprising:
capturing reference characteristic data from the one or more reference objects of authentication;
deriving the reference authentication data from the reference characteristic data of the one or more reference objects of authentication; and
storing the reference authentication data in the electronic database.

8. The method of claim 7, deriving the reference authentication data from the reference characteristic data comprising analyzing the reference characteristic data using one or more of: an image transform, statistical analysis, principle component analysis, optical character recognition analysis, font reconstruction, image analysis, polynomial spline fitting, Bezier curve spline fitting, Bezier curve extraction/characterization, Scalable Vector Graphic analysis, Unified Font Object analysis, image registration, wavelet analysis, and spatial frequency analysis.

9. The method of claim 1, further comprising reporting the authentication score, the authentication score comprising one or more of: a Boolean value, a binned value, and a probability.

10. The method of claim 1:
capturing the characteristic data comprising capturing an optical image of markings on the object of authentication;
deriving the authentication data comprising providing the optical image of the markings for the comparing;
the reference authentication data comprising at least one reference authentication image corresponding to the one or more reference objects of authentication, comparing the authentication data with the electronic database comprising determining a mathematical similarity or difference between the optical image of the markings and the at least one reference authentication image to provide the authenticity score for the object of authentication, the authenticity score indicating whether the object of authentication has a same origin of manufacture as the one or more reference objects of authentication.

11. A tangible computer-readable medium having instructions stored thereon for controlling a processor, the instructions controlling the processor to:
operate a characterization module comprising a measurement system to capture characteristic data from an object of authentication, capturing the characteristic data comprising capturing an optical image of the object of authentication;
derive authentication data from the characteristic data of the object of authentication deriving the authentication data comprising:
performing optical characterization recognition and font reconstruction of the optical image to provide a reconstructed font, and
extracting from the reconstructed font one or more parameters of a polynomial spline or a Bezier curve spline representative of the reconstructed font to provide the authentication data comprising a spline font database, the authentication data comprising the spline font database corresponding to marking system data;
compare the authentication data with an electronic database comprising reference authentication data to provide an authenticity score for the object of authentication, the reference authentication data corresponding to one or more reference objects of authentication other than the object of authentication, the reference authentication data comprising reference marking system data, comparing the authentication data with the electronic database comprising comparing the marking system data with the reference marking system data to provide the authenticity score for the object of authentication, the reference marking system data: corresponding to a marking system used to mark the one or more reference objects of authentication; and being derived from statistical testing of the reference authentication data; and access a data storage module to store and retrieve one or more of: the authentication data, the electronic database comprising the reference authentication data corresponding to one or more reference objects of authentication other than the object of authentication, the characteristic data from the object of authentication, and the authenticity score;

the instructions being configured to control the processor comprising one or more of: a local processor, an embedded processor, a distributed processor, a smart phone, a smart watch, a personal computer; and a tablet computer;

the instructions being configured to control the processor to access the data storage comprising one or more of: a memory operatively coupled to the processor and a remote storage system operatively coupled to the processor; and the instructions being configured to control the measurement system comprising one or more of: an imager, a profilometer, a scatterometer, a polarimeter, and a microscope.

12. The tangible computer-readable medium of claim 11, the instructions for controlling the processor further comprising instructions configured to control the measurement system comprising a spectrometer.

* * * * *